a2

US008574543B2

(12) United States Patent
Lee et al.

(10) Patent No.: US 8,574,543 B2
(45) Date of Patent: Nov. 5, 2013

(54) METHOD OF ISOTOPE LABELING AND DETERMINING PROTEIN SYNTHESIS, QUANTITATION AND PROTEIN EXPRESSION

(75) Inventors: Wai-Nang P. Lee, Palos Verdes Estates, CA (US); Guishim Xiao, Rolling Hills Estates, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 799 days.

(21) Appl. No.: 12/333,240

(22) Filed: Dec. 11, 2008

(65) Prior Publication Data

US 2009/0176199 A1 Jul. 9, 2009

Related U.S. Application Data

(60) Provisional application No. 61/013,804, filed on Dec. 14, 2007.

(51) Int. Cl.
*A61K 51/00* (2006.01)

(52) U.S. Cl.
USPC ..................................... 424/1.69; 424/1.65

(58) Field of Classification Search
USPC ............................................... 424/1.69, 1.65
See application file for complete search history.

(56) References Cited

FOREIGN PATENT DOCUMENTS

WO    WO 03/061479 A1    7/2003
WO    WO 2005/051434 A1    6/2005

OTHER PUBLICATIONS

Gardner et al. "Measurement of liver collagen synthesis by heavy water labeling: effects of profibrotic toxicants and antifibrotic interventions", Am J Physiol Gastrointest Liver Physiol., 2007, 292:G1695-G1705.*
Fanara et al. "In vivo measurement of microtubule dynamics using stable isotope labeling with heavy water", JBC, 2004, 279(48):49940-49947.*
Weatherly et al. "A heuristic method for assigning a false-discovery rate for protein identifications from Mascot database search results", Molesular & Cellular Proteomics, 2005, 4:762-772.*
Bateman, R. J. et al., "Human amyloid-beta synthesis and clearance rates as measured in cerebrospinal fluid in vivo", Nature Medicine, 12 (7), (Jul. 2006), 856-861.
Bateman, R. J. et al., "Stable isotope labeling tandem mass spectrometry (SILT) to quantify protein production and clearance rates", J Am Soc Mass Spectrom, 18 (6), (Jun. 2007), 997-1006.
Beynon, R. J. et al., "Metabolic Labeling of Proteins for Proteomics", Molecular & Cellular Proteomics 4.7, (2005), 857-872.
Blom, K. F., "Average Mass Approach to the Isotopic Analyses of Compounds Exhibiting Significant Interfering Ions", Anal. Chem. 60, (1988), 966-971.

Bouwman, F. et al., "A combination of protein profiling and isotopomer analysis using matrix-assisted laser desorption/ionization-time of flight mass spectrometry reveals an active metabolism of the extracellular matrix of 3T3-L1 adipocytes", Proteomics, 4, (2004), 3855-3863.
Busch, R. et al., "Measurement of protein turnover rates by heavy water labeling of nonessential amino acids", Biochim Biophys Acta, 1760, (2006), 730-744.
Cargile, B. J. et al., "Synthesis/Degradation Ratio Mass Spectometry for Measuring Relative Dynamic Protein Turnover", Anal. Chem. 76, (2004), 86-97.
Doherty, M. K. et al., "Proteome dynamics in complex organisms: Using stable isotopes to monitor individual protein turnover rates", Proteomics, 5, (2005), 522-533.
Fern, E. B. et al., "The Specific Radioactivity of the Tissue Free Amino Acid Pool as a Basis for Measuring the Rate of Protein Synthesis in the Rat in vivo", Biochem. J., 142, (1974), 413-419.
Gan, C. S. et al., "Technical, Experimental, and Biological Variations in Isobaric Tags for Relative and Absolute Quantitation (iTRAQ)", Journal of Proteome Research, 6, (2007), 821-827.
Gygi, S. P. et al., "Quantitative analysis of complex protein mixtures using isotope-coded affinity tags", Nature Biotechnology, 17, (Oct. 1999), 994-999.
Hellerstein, M. K. et al., "Mass isotopomer distribution analysis at eight years: theoretical, analytic, and experimental considerations", Am J Physiol Endocrinol Metab, 276, (1999), 1146-1170.
Hellerstein, M. K. "Relationship Between Precursor Enrichment and Ratio of Excess $M_2$/Excess $M_1$ Isotopomer Frequencies in a Secreted Polymer", Journal of Biological Chemistry, vol. 266, No. 17, (Jun. 15, 1991), 10920-19024.
Jennings, M. E., et al., "Determination of Complex Isotopomer Patterns in Isotopically Labeled Compounds by Mass Spectrometry", Analytical Chemistry, 77 (19), (Oct. 1, 2005), 6435-6444.
Katz, J. et al., "Studies of Glycogen Synthesis and the Krebs Cycle by Mass Isotopomer Analysis with [U-$^{13}$C]Glucose in Rats", Journal of Biological Chemistry, 264 (22), (Aug. 5, 1989), 12994-13001.
Lee, W. N. Paul et al., "In vivo measurement of fatty acids and cholesterol synthesis using $D_2O$ and mass isotopomer analysis", Am J Physiol, 266, (1994), E699-E708.
Lee, W. N. Paul et al., "Mass Isotopomer Analysis: Theoretical and Practical Considerations", Biological Mass Spectrometry, 20, (1991), 451-458.
Lee, W. N. Paul et al., "Mass Isotopomer Pattern and Precursor-Product Relationship", Biological Mass Spectrometry, 21, (1992), 114-122.

(Continued)

*Primary Examiner* — Bin Shen
(74) *Attorney, Agent, or Firm* — Blakely Sokoloff Taylor & Zafman LLP

(57) ABSTRACT

A method including isotope labeling of a newly synthesized protein in a sufficient quantity such that a newly synthesized protein spectra and the pre-existing protein spectra are sufficiently separated. A further method including determining a ratio of a new and a pre-existing protein from mass spectra obtained by using mass spectrometry. In this method a resultant spectrum may be presented as integrated peak heights for a corresponding mass to charge ratio in the "centroid" mode.

7 Claims, 17 Drawing Sheets

(56) References Cited

OTHER PUBLICATIONS

Lee, W. N. Paul et al., "Measurement of fractional lipid synthesis using deuterated water ($^2H_2O$) and mass isotopomer analysis", Am J Physiol, 266, (1994), E372-E383.

Mann, M. et al., "Analysis of Proteins and Proteomes by Mass Spectrometry", Annu. Rev. Biochem., 70, (2001), 437-473.

Merkwirth, C. et al., "Prohibitins control cell proliferation and apoptosis by regulating OPA1-dependent cristae morphogenesis in mitochondria", Genes & Development, 22, (2008), 476-488.

Ong, S. E., "Stable Isotope Labeling by Amino Acids in Cell Culture, SILAC, as a Simple and Accurate Approach to Expression Proteomics", Molecular & Cellular Proteomics 1.5, (May 2002), 376-386.

Papageorgopoulos, C. et al., "Measuring Protein Synthesis by Mass Isotopomer Distribution Analysis (MIDA)", Analytical Biochemistry, 267, (1999), 1-16.

Papageorgopoulos, C. et al., "Measuring synthesis rates of muscle creatine kinase and myosin with stable isotopes and mass spectrometry", Analytical Biochemistry, 309, (2002), 1-10.

Pratt, J. M. et al., "Dynamics of Protein Turnover, a Missing Dimension in Proteomics", Molecular & Cellular Proteomics 1.8, (2002), 579-591.

Previs, S. F. et al., "Quantifying rates of protein synthesis in humans by use of $^2H_2O$: application to patients with end-stage renal disease", Am J Physiol Endocrinol Metab, 286, (2004), E665-E672.

Pupim, L. B. et al., "Nutritional Supplementation Acutely Increases Albumin Fractional Synthetic Rate in Chronic Hemodialysis Patients", J Am Soc Nephrol, 15, (2004), 1920-1926

Raj, D. S. et al., "Glutamine kinetics and protein turnover in end-stage renal disease", Am J Physiol Endocrinal Metab, 288, (2005), E37-E46.

Russell, W. K. et al., "Proteolysis in Mixed Organic-Aqueous Solvent Systems: Applications for Peptide Mass Mapping Using Mass Spectometry", Anal. Chem., 73 (11), (2001), 2682-2685.

Shi, Y. E. et al., "Expression of 67 kDa laminin receptor in human breast cancer cells: regulation by progestins", Clinical & Experimental Metastasis, 11 (3), (1993), 251-261.

Tessari, P. et al., "Postprandial body protein synthesis and amino acid catabolism measured with leucine and phenylalanine-tyrosine tracers", Am J Physiol Endrocrinol Metab, 284, (2003), 1037-1042.

Vogt, J. A. et al., "Determination of Fractional Synthesis Rates of Mouse Hepatic Proteins via Metabolic C-Labeling, MALDI-TOF MS and Analysis of Relative Isotopologue Abundances Using Average Masses", Anal. Chem., 77 (7), (2005), 2034-2042.

Vogt, J. A. et al., "Protein abundance quantification in embryonic stem cells using incomplete metabolic labelling with $^{15}N$ amino acids, matrix-assisted laser desorption/ionisation time-of-flight mass spectrometry, and analysis of relative isotopologue abundances of peptides", Rapid Communications in Mass Spectrometry, 17, (2003), 1273-1282.

Wang, B. et al., "Isotopologue distributions of peptide product ions by tandem mass spectrometry: Quantitation of low levels of deuterium incorporation", Analytical Biochemistry, 367, (2007), 40-48.

Washburn, M. P. et al., "Large-scale analysis of the yeast proteome by multidimensional protein identification technology", Nature Biotechnology, 19, (Mar. 2001), 242-247.

Williams, D. B., "Beyond lectins: the calnexin/calreticulin chaperone system of the endoplasmic reticulum", Journal of Cell Science, 119, (2006), 615-623.

Wolfe, R. R., Radioactive and Stable Isotope Tracers in Medicine. New York: Wiley-Liss, (1992), 377-416.

Wu, C. C. et al., "Metabolic Labeling of Mammalian Organisms with Stable Isotopes for Quantitative Proteomic Analysis", Analytical Chemistry, 76 (17), (Sep. 1, 2004), 4951-4959.

Xiao, G. G. et al., "Determination of protein synthesis in vivo using labeling from deuterated water and analysis of MALDI-TOF spectrum", J. Appl. Physiol., 104, (2008), 828-836.

Xiao, G. G, et al., "Use of Proteomics to Demonstrate a Hierarchical Oxidative Stress Response to Diesel Exhaust Particle Chemicals in a Macrophage Cell Line", Journal of Biological Chemistry, vol. 278, No. 50, (Dec. 12, 2003), 50781-50790.

LA Biomed, "International Search Report and Written Opinion," dated Jan. 13, 2010 for PCT/US2008/086710.

LA Biomed, "International Preliminary Report on Patentability," dated Jun. 24, 2010 for PCT/US2008/086710.

* cited by examiner

Leu-d3
Non-Dialyzed Serum

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Val Glu Gly Gly Gln His Leu Asn Val Met Val Leu Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

His Pro Asp Tyr Ser Val Ser Leu Leu Leu Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Met Pro Leu Phe Lys Leu Thr Glu Ile Asp Asp Ala Met
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 4

Leu Gly Glu Tyr Gly Phe Gln Asn Ala Ile Leu Val Arg
1               5                   10

<210> SEQ ID NO 5
<211> LENGTH: 13
<212> TYPE: PRT
<213> ORGANISM: Artificial Sequence
<220> FEATURE:
```

```
<223> OTHER INFORMATION: Synthetic Peptide

<400> SEQUENCE: 5

Asp Val Phe Leu Gly Thr Phe Leu Tyr Glu Tyr Ser Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Ile Glu Glu Asn Gly Ser Met Arg
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Phe Thr Pro Gly Thr Phe Thr Asn Gln Ile Gln Ala Ala Phe Arg
1               5                   10                  15
```

METHOD OF ISOTOPE LABELING AND DETERMINING PROTEIN SYNTHESIS, QUANTITATION AND PROTEIN EXPRESSION

CROSS REFERENCE TO RELATED APPLICATIONS

This application claims priority from U.S. Provisional Patent Application Ser. No. 61/013,804, filed on Dec. 14, 2007.

SEQUENCE LISTING

An electronic copy of the Sequence Listing entitled "P012_SeqList.txt" is herein incorporated by reference. This Sequence Listing consists of [SEQ. ID NOs: 1-7].

BACKGROUND

1. Field

Techniques for tracking the turnover of a proteome by randomly labeling of proteins with stable isotopes $^{13}C$, $^{2}H$ and $^{15}N$ (carbon-13, deuterium and nitrogen-15) for the purpose of examining the dynamics of a system of proteins within an organism (e.g. a cell, whole animal or patient) in response to various drugs. The information obtained by such a method permits the determination of the organism's physiology based on the turnover and expression (i.e., relative concentration) of cellular proteins such as enzymes and membrane proteins, which often are the target of drugs or biological agents.

2. Background

The Human Genome Project has enabled the discovery of proteins, and the identities of their structures. However, the presence of a gene or its expression in a cell in the form of messenger RNA often does not correlate with the concentration of its translational product (protein), nor its function as affected by post-translational modifications. Therefore, the knowledge of a protein's concentration within a cell, its "expression" and modification, is critical to the understanding of cellular physiology and the molecular effects of therapeutic agents.

The concentration of a protein in a cell depends on the rate of its synthesis and degradation. Thus, the rate of protein turnover, the time required to synthesize a certain protein and maintain its concentration in a cell, is a sensitive indicator of cell physiology or its phenotype. The rate of protein turnover reflects a cell's response to 1) nutrient environment, 2) cell signaling due to growth factors and hormones including cytokines, 3) transcriptional regulators to differentiate or proliferate, and 4) drugs which may act in a way similar to any of the foregoing three factors.

Protein turnover is usually expressed as the rate of protein synthesis (in moles/unit time) or its half-life, which is the time required to achieve half of the maximum concentration of the protein for a given rate of protein synthesis. The determination of protein synthesis and turnover has been of great interest to biologists who are interested in understanding cellular physiology and phenotype.

Radioactive and stable isotope tracers have been used for the determination of protein synthesis and turnover for more than two decades. The basic principle of protein turnover measurement using tracers relies on the measurement of the specific activity of the "precursor" (or the labeling agent, which can be deuterium in deuterated water, or specifically labeled amino acids such as [1-$^{13}$C]-leucine, [5,5,5-$^{2}$H$_{3}$]-leucine) and the determination of the specific activity (SA) or enrichment (E) of the labeling agent (precursor) in the protein. The newly synthesized fraction (FNP), also referred to as FNS (fraction of new synthesis), is provided by the formula:

FNP=[SA or E of the precursor in protein]/[SA or E of the precursor]

Protein synthesis rate (PSR), also referred to herein as FSR (fractional synthesis rate), is calculated by dividing the quantity of new protein by the time interval for the change using the equation:

PSR=[protein concentration]×(FNP)/(unit time)

When FNP or PSR are obtained for multiple time points, FNP or PSR can be plotted against time for the estimation of half-life of the turnover of the protein using compartmental analysis. An example of a rate equation for a single compartment is $FNP(t)=1-FNP(max)\times e^{-kt}$ where k is the fraction that is cleared (turned over) per unit time. From k, $t_{1/2}$ can be calculated. (see FIG. 1).

Examples of application of such a principle for the determination of protein synthesis and turnover using tracers have been published by Wolfe R R. *Radioactive and Stable Isotope Tracers in Medicine*. New York: Wiley-Liss, 377-416, 1992.

In order to satisfy the conditions required for calculation of FNP as previously described, the enrichment or specific activity of the labeled precursor has to be unique. The label should not be lost or gained in the process of protein synthesis, protein isolation or protein hydrolysis. Some of the more frequently used labeled amino acids are L-[1-$^{14}$C]leucine or L-[1-$^{13}$C]leucine, L-[ring-$^{2}$H$_{5}$]phenylalanine ([$^{2}$H$_{5}$]Phe) and L-[$^{2}$H$_{2}$]tyrosine ([$^{2}$H$_{2}$]Tyr), and L-[ring-$^{2}$H$_{4}$]tyrosine ([$^{2}$H$_{4}$] Tyr as described in Tessari P, et al., *Postprandial body protein synthesis and amino acid catabolism measured with leucine and phenylalanine-tyrosine tracers*. Am J Physiol Endocrinol Metab. 2003.

A labeling method using deuterated water ($D_2O$) or heavy water in the determination of protein synthesis was introduced by, for example, Previs F., et al. *Quantifying rates of protein synthesis in humans by use of $^{2}H_{2}O$: application to patients with end-stage renal disease*. Am J Physiol Endocrinol Metab 286: E665-E672, 2004 referred to herein as Previs et al., (2004) and Busch R, et al. *Measurement of protein turnover rates by heavy water labeling of nonessential amino acids*. Biochim Biophys Acta. 2006 May; 1760 (5):730-44 referred to herein as Busch et al. (2006) or Hellerstein.

These methods rely on the incorporation of deuterium into non-essential amino acids (NEAA) such as alanine, glycine and glutamate in living cells.

FIG. 2 shows the incorporation of deuterium or nitrogen into non-essential amino acids (NEAA) through transamination. In this figure, heavy isotopes of hydrogen (H) are shown in bold and light isotopes are shown in standard font. Since low enrichments of the isotopes are used, the heavy atom only indicates the position within the molecule that has a probability of being labeled. During the transamination process, amino acids are deaminated forming a keto-acid. The carbonyl group in the keto acid accepts a nitrogen donor from ammonium ion ($^{15}NH_4^+$) of N-15 isotope. In subsequent reduction, the amino acid is labeled with N-15. If the reaction takes place in medium containing deuterium, the reduction process labels the amino acid with deuterium. Deuterium can also be incorporated into gluconeogenic amino acids through reduction and oxidation reactions which are not shown.

FIG. 3 shows the incorporation of $^{13}$C from [U$^{13}$C$_6$]-glucose. Glucose is a major carbon source in the synthesis of non-essential amino acids. In this figure, heavy isotopes of carbon (C) are shown in bold and light isotopes are shown in standard font. Since low enrichments of the isotopes are used, the heavy atom only indicates the position within the molecule that has a probability of being labeled. The labeling of alanine, aspartate, glutamate and glycine are illustrated. Alanine is formed from pyruvate which is a product of glycolysis. The pattern of labeling in aspartate and glutamate reflects the action of the TCA cycle. When the enrichment of $^{13}C$ in glucose is low, the probability of mass isotopomers formation in these amino acids is reduced. These amino acids will contain on average mostly singly labeled (m1) species.

When cells or animals are given deuterium water, it is possible to maintain a high level of enrichment in water (0.5-2%). Previs et al. (2004) showed that plasma alanine rapidly incorporated the deuterium from water changing its $CH_3$— group to $CD_3$- thus increasing its molecular weight by three daltons. The actual increase in molecular weight is less due to the low level of enrichment of deuterium water used. The enrichment in alanine can be determined by gas chromatography/mass spectrometry (GC/MS) after derivatization. When a specific protein such as albumin is isolated and hydrolyzed, the enrichment in alanine isolated from the protein can be similarly determined by GC/MS. FNP can be calculated using the previously described FNP equation. The method of Hellerstein (Busch et al., 2006) differs from the method of Previs et. al. (2004) in that he used a different experimental approach to determine amino acid enrichment using mass isotopomer distribution analysis (MIDA). It should be noted that these methods are variations of the basic precursor/product enrichment ratio method previously described. They all require 1) determination of precursor SA or E, 2) isolation of specific protein of interest, 3) hydrolysis of the protein to separate the amino acids, 4) determining the enrichment in the specific amino acid of interest, and 5) application of the equations previously described. In this approach, however, any contamination of the protein in the isolated protein will alter the isotope enrichment of the amino acid in the hydrolysate therefore the accuracy of the determined FNP in such a determination is in doubt.

With the advent of high resolution maximum mass spectrometer capable of resolving molecules with molecular weights (m/z)>1000 daltons, other isotope labeling approaches have been devised to quantify proteins, determine relative protein expression and determine protein synthesis. Generally, these methods have only been applied to studies in cell culture and in yeast. The use of such methods in the quantitation of proteins has been reviewed in Beynon R J et al. *Metabolic labeling of proteins for proteomics. Mol Cell Proteomics.* 2005; 4(7):857-72 referred to herein as Beynon (2005).

These methods are used in the determination of (i) relative quantities (expression), (ii) protein identification, and (iii) protein turnover (synthesis).

Carbon, hydrogen, oxygen and nitrogen are the elements of organic compounds. In primitive organisms such as bacteria and yeast, organic compounds such as amino acids can be synthesized from simple molecules such as carbon dioxide and ammonia. In higher organisms such as multicellular organisms, such synthetic capability is lost. In order to introduce stable isotopes $^{13}C$, $^{2}H$ and $^{15}N$ (carbon-13, deuterium and nitrogen-15, respectively), other precursors such as $[U^{13}C_6]$-glucose, $[^{15}N, ^{13}C]$-amino acids or deuterated amino acids must be used. The application of amino acids such as L-$[5,5,5-^{2}H_3]$leucine results in incremental mass shifts of +3 daltons in proteins. Examples of applications of highly enriched labeled amino acids in proteomics are provided in the review by Beynon (2005).

One of the reasons for using heavily labeled amino acids such as L-$[^{13}C_6]$arginine to introduce stable isotopes into proteins is to separate the labeled protein from the unlabeled one by mass spectrometry such that there is no or little overlap between the spectra of these two protein species. If a lower enrichment of a fully labeled amino acid is used, it is possible to have multiple isotopomer peaks, and the information from such a spectrum is difficult to interpret.

FIG. 4 shows shifts in a peptide containing three leucines as described in Ong et al., Mol Cell Proteomics. 2002 May; 1(5):376-86 referred to herein as Ong et al. (2002). NIH3T3 cells were incubated in medium containing non-dialysed serum resulting in partially enriched d3-leucine. The mass spectrum of FIG. 4 is shown in profile of continuous distribution of molecular weights. In the synthesis of the MW 652.04 peptide, 1, 2 or 3 d3-leucines are incorporated resulting in mass shifts of +3, +6 and +9 daltons. Because the peptide in the spectrum has three positive charges, the mass shifts appear to as m/z+1, +2 and +3. However, when cells were incubated with 99% enriched d3-leucine with dialysed serum, only +9 molecular species was observed. (see FIG. 5) The mass spectrum of this peptide is complicated by the existence of an isotope envelope due to natural abundance of $^{13}C$, $^{18}O$ and $^{15}N$ and by contamination by other peptides.

Stable isotope labeling with amino acids in cell culture (SILAC) is a technique for labeling proteins with a labeled essential amino acid for the determination of protein expression (relative concentration of proteins in experimentally treated and control cells). In the SILAC method, proteins are completely labeled in cell cultures using fully labeled essential amino acids (for example d3-leucine, $^{15}N$-$^{13}C$-arginine, etc. (www.silac.org)). Cells are grown for several days (after several cell divisions) until the corresponding essential amino acid in proteins is completely replaced with the labeled essential amino acids. These fully labeled proteins are then used as reference standard to determine changes in protein expression in these cells after molecular manipulation. This approach allows the determination of changes in protein expression levels (concentrations) of many cellular proteins by determining the mass spectral peaks corresponding to the unlabeled (from manipulated cells) to labeled (from control) protein. Protein expression is provided by the following formula:

Protein expression=[unlabeled peak]/[labeled peak]

A ratio of one means that a protein is neither under nor over expressed. A ratio of <1 means under-expression (concentration is less than that of the control) and >1, over-expression (concentration is greater than that of the control).

FIG. 5 shows mass shifts in a peptide containing d3-leucine (from Ong et al. 2002). NIH3T3 cells were incubated in medium containing 99% d3-leucine and dialysed serum for 24 hour. In the synthesis of the MW 652.04 peptide, d3-leucines are incorporated resulting in a mass shift of m/z+3 in the spectrum (actually +9 daltons as previously discussed). In subsequent discussion, this peak is designated as d3. In 24 hours, some unlabeled (unenriched) peptide remained. By adding a known amount of protein from cells grown in $[5,5,5^{2}H_3]$ leucine, the relative protein expression is given by the ratio of d3/d0 when the d0 and d3 peaks are compared as the "unlabeled" and the "labeled" peaks. The other relevant peaks of the spectrum are ignored. Since the exact precursor enrichment is not known, protein synthesis cannot be determined.

Attempts have been made to determine protein synthesis in vivo using mass isotopomer distribution analysis (MIDA) as an extension of the same method in the determination of synthesis of polymers. See, for example, Papageorgopoulos C, et al. *Measuring protein synthesis by mass isotopomer distribution analysis (MIDA)*. Anal Biochem. 1999 Feb. 1; 267(1):1-16 and Hellerstein M K, Neese R A. *Mass isotopomer distribution analysis at eight years: theoretical, analytic, and experimental considerations*. Am J. Physiol. 1999 June; 276(6 Pt 1):E 1146-70. Doherty M K et al. *Proteome dynamics in complex organisms: using stable isotopes to monitor individual protein turnover rates*. Proteomics. 2005 February; 5(2):522-33.

In these demonstrations, rats were infused with $[5,5,5-^2H_3]$ leucine (99% enriched) via the jugular catheter for 24 h using a minipump at a rate of ~50 mg/kg/h. Muscle was harvested and creatine kinase (CK) was isolated. Trypsin digest of the protein was analysed using an electrospray ionization/magnetic sector mass spectrometer. Mass isotopomers containing leucine isotope in peptides rich in leucine was determined. Incorporation of $[5,5,5-^2H_3]$leucine would result in mass shift of +3, +6, etc. depending on the number of leucine in the peptide and the enrichment of intramyocyte leucine. However, due to the low protein turnover rate, the +3 or +6 isotopomers were not detected. Even though MIDA method is theoretically possible in such application, the feasibility of the MIDA method as described by Papageorgopoulos C, Caldwell K, Schweingrubber H, Neese R A, Shackleton C H, Hellerstein M. *Measuring synthesis rates of muscle creatine kinase and myosin with stable isotopes and mass spectrometry*. Anal Biochem. 2002 Oct. 1; 309(1): 1-10 referred to herein as Papageorgopoulos et al. (2002) for in vivo study was not demonstrated.

Determination of low levels of deuterium incorporation into peptides from deuterated water was recently described by Wang et al. (Wang B, Sun G, Anderson D R, Jia M, Previs S, Anderson V E. *Isotopologue distributions of peptide product ions by tandem mass spectrometry: quantitation of low levels of deuterium incorporation*. Anal Biochem. 367(1):40-8, 2007) by determining excess molar ratio at M1 (peptide with one deuterium incorporated). However, such an approach using excess mass calculation is similar to the excess M1 calculation of Hellerstein (Hellerstein M K. *Relationship between precursor enrichment and ratio of excess M2/excess M1 isotopomer frequencies in a secreted polymer*. Biol. Chem. 266(17):10920-4, 1991), and cannot be used to determine protein synthesis without additional information of the isotopomer distribution of the new peptide.

Another method using mass spectrum for the determination of protein synthesis is that of Cargile B J, et al. (*Synthesis/degradation ratio mass spectrometry for measuring relative dynamic protein turnover*. Anal Chem. 2004 Jan. 1; 76(1):86-97) referred to herein as Cargile et al. (2004). The method introduces $^{13}C$ carbon into protein by substituting natural glucose with $[U^{13}C_6]$-glucose (final enrichment>50%). In organisms which can synthesize essential and non-essential amino acids from glucose and nitrogen, $[U^{13}C_6]$-glucose effectively replaces $^{12}C$ by $^{13}C$ in protein creating a heavy protein which can be separated by mass spectrometry. By quantitating the intensity of the labeled and the unlabeled peaks, a synthesis/degradation ratio can be calculated to represent relative dynamic protein turnover. Such a method is useful for the study of organisms such as bacteria and yeast, which can synthesize their amino acids from glucose and nitrogen.

FIG. 6 shows the labeling of protein with highly enriched $[U^{13}C_6]$glucose (see Ong et al., 2002) *E. coli* strain was grown in minimal medium with $[U^{13}C_6]$glucose as the carbon source. MALDI-TOF/TOF spectrum of peptide VEGGQHL-NVMVLR [SEQ ID NO: 1] shows well separated labeled and unlabeled peaks of $^{12}C$ and $^{13}C$ peptides. The mathematical model (approximation with a Poisson distribution) is applicable only with $^{12}C$ and $^{13}C$ peptides, i.e., the model does not resolve overlapping ions.

BRIEF DESCRIPTION OF DRAWINGS

The subject matter disclosed herein is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Techniques for the determination of protein synthesis and turnover using $^{13}$C, $^{15}$N and $^{2}$H labeling and protein mass spectra are disclosed. It is known that metabolic systems in cells of organisms are capable of synthesizing non-essential amino acids. In the process of amino acid synthesis, carbon, nitrogen and hydrogen atoms are incorporated from their precursor substrates either directly or through exchanges (transamination). If these precursor substrates are enriched with one or more of these isotopes, the resultant amino acids are heavier than the "natural" amino acids. Protein molecules that are synthesized after the introduction of the heavy isotopes will contain the heavier amino acids resulting in a mass shift in the corresponding spectrum.

Figure 7:
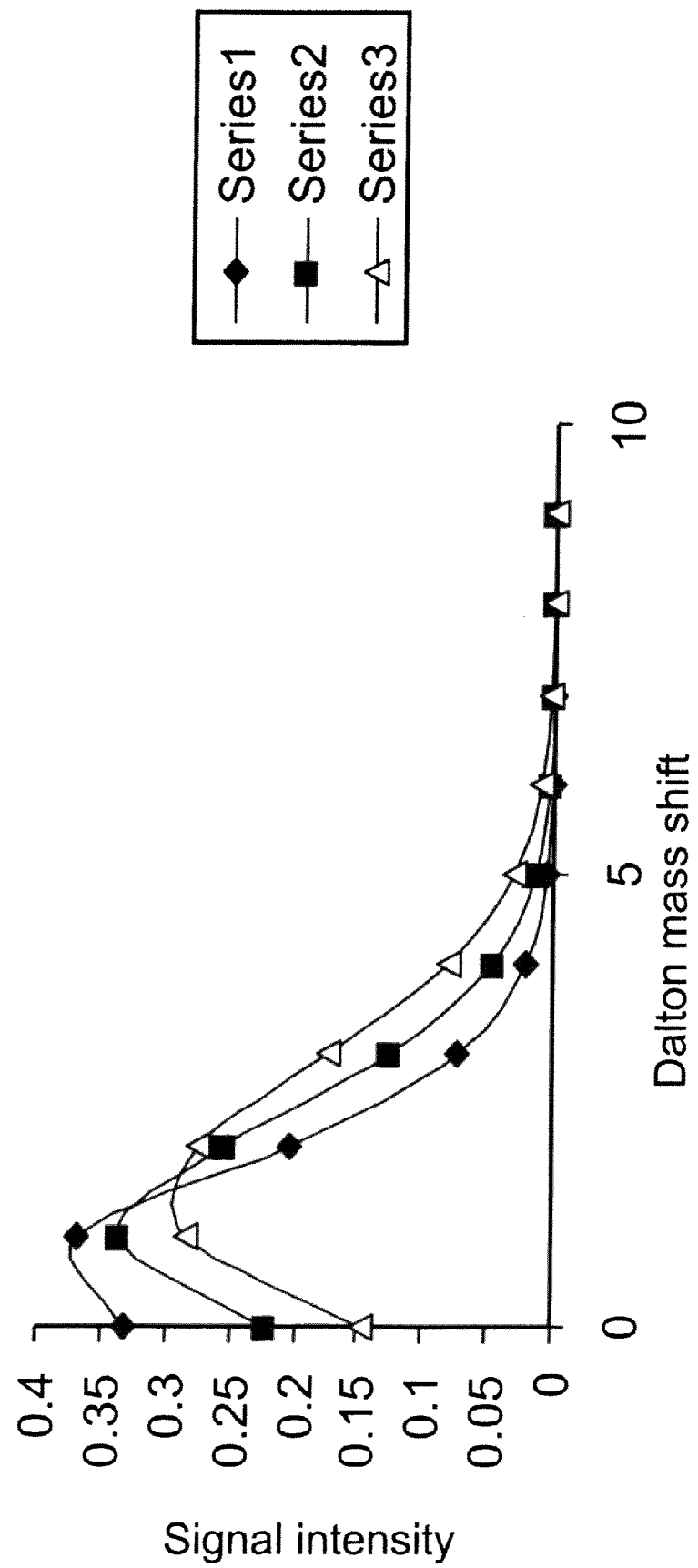
FIG. 7 shows overlapping peaks of mass spectra (mass isotopomers) of heavy and light proteins due to deuterium incorporation. Series 1 is that of the unlabeled protein. Series 2 and 3 are spectra of the lightly labeled proteins.

FIG. 7 shows overlapping peaks of mass spectra (mass isotopomers) of heavy and light protein due to deuterium incorporation. The introduction of deuterium into amino acids of the newly synthesized protein results in a small but measurable mass shift. The mass shift depends on the number of exchangeable protium ion and the enrichment of deuterium in water. The theoretical mass isotopomer distribution of a peptide with 100 carbon and 20 exchangeable protium atoms is shown in series 1. When the protium atoms are substituted at random by deuterium at 2% and 4% enrichment, the mass isotopomer distributions are shifted (series 2 and 3). By fitting the mass isotopomer distribution curves to model a mixture of light and heavy protein from a certain deuterium environment, the contribution of these two species can be resolved using multiple linear regression analysis. The x-axis is in dalton mass shift from the monoisotopic species (m0). The scale of the axis is in integer increments (1, 2, 3, etc.).

The intensities of the mass peaks corresponding to the unlabeled (light) and the labeled (heavy) can be used for calculation of the newly synthesized fraction. This approach differs from that of SILAC, in that intensities of relevant peaks in the spectrum are used for the calculation of protein turnover while only prominent peaks d0 and d3 are used in SILAC as in the example of Ong et al. (2002).

The method described herein differs from previous methods in that it utilizes the individual and cumulative intensities of the peptide spectrum instead of the intensities of unique mass peaks. The mass spectral peaks of the heavier protein are resolved from the lighter (natural) protein by mathematical simulation. The capability of resolving overlapping spectra makes it possible to label proteins with lower enrichment of stable isotopes. The need for highly enriched precursor substrates is obviated.

There are major differences distinguishing techniques disclosed herein from previous methods. The present method differs from those of Previs et al. (2004) and Papageorgopoulos et al. (2002) in that 1) determination of isotope enrichment in a specific amino acid in a protein is not required and 2) fraction of new protein is determined from the mass spectrum of the protein or its fragments after enzyme digestion. The techniques disclosed herein do not use the FNP calculation previously discussed. Rather, the approach disclosed herein is based on the concept that mass isotopomer distribution in the newly synthesized protein due to isotope incorporation is a concatenation of $^{13}$C isotopomers from $^{13}$C natural abundance with $^{2}$H isotopomers. In general, a molecule of protein is made of many atoms of carbon, hydrogen, nitrogen, and oxygen, the probability of a protein molecule having one or more of the heavy isotope generates an isotopomer distribution reflected by the isotope envelope. Since the natural abundance of $^{13}$C is much greater than the natural abundance of either nitrogen or oxygen, the isotopomers of a natural (unlabeled) peptide is approximated by $^{13}$C isotopomers and are referred to as $^{13}$C isotopomers. Since $^{13}$C isotopomers is known, the $^{2}$H isotopomer distribution can be determined from the observed spectrum using the inverse concatenation operation. FNP can be determined by comparing the theoretical and the observed $^{2}$H isotopomer distribution using regression analysis. Alternatively, fraction of new protein synthesis (FNP) is provided by the ratio of the old and new isotopomer distributions. This is different from that of Previs et al. (2004) in that enrichment of $^{2}$H in amino acids as well as that in the peptide is determined separately and the FNP is given by the enrichment of the amino acid in the protein divided by the enrichment of the amino acid in the plasma.

The techniques disclosed herein further differ from that of Cargile et al. (2004) in $^{12}$C with $^{13}$C in proteins do not need to be completely replaced to eliminate overlapping labeled and unlabeld peaks. Overlapping labeled and unlabeled peaks are resolved by a mathematical algorithm.

The techniques disclosed herein provide an early detection means or test for determining changes in protein turnover and protein concentration in response to a therapeutic intervention. The methodology is applicable to measuring protein synthesis/turnover in cell culture or in whole organism such as an animal or person. By virtue of the importance of protein turnover in biological function, the measurement can be used to predict an outcome (i.e., risk or benefit) of a therapeutic intervention such as a drug treatment (e.g., cancer drug treatment). For example, if a protein turnover rate in the cancer cell is found to be suppressed upon the administration of a drug, the drug can be determined to be potentially effective against such a cancer. The protein turnover rate can also be used to differentiate protein secreted by normal cells from malignant cells. Thus, the labeling of protein can also be used for biomarker discovery.

It has unexpectedly been found that proteins can be labeled with low levels of enrichment of stable isotopes $^{13}$C, $^{2}$H and $^{15}$N (carbon-13, deuterium and nitrogen-15) such that there is a measurable mass shift in the newly synthesized proteins. Using techniques described herein, the labeled proteins and their unlabeled (natural) counterparts can be quantified using mass spectrometry. In contrast to methods which require isotope enrichment of >98%, the techniques described herein utilize lower levels of isotope enrichment-deuterated water (deuterium enrichment of 2-3%), [U$^{13}$C$_6$]glucose ($^{13}$C enrichment of 30-50%) or [$^{15}$N]-amino acid mixture ($^{15}$N enrichment of 10-20%). Even lower enriched precursors can be used depending on the precision and accuracy of the obtained mass spectra.

Techniques disclosed herein further differ from previous methods in that intensities of all isotopomers can be used in the determination of FNP and PSR and a reference protein with PSR (or FSR) close to 100% is not required. To contrast in particular, in one method disclosed by Vogt et. al. *Rapid Commun. Mass Spectrom.* 2003, 17, 1273-82 referred to herein as Vogt (2003), estimation of FSR is based on comparing the change in average mass of proteins with the change in average mass of the same proteins when FSR is close to 100%. In this method the observed average mass is the weighted sum of the mass isotopomers (mass shift) of the peptide.

$$FSR = (\text{change in average mass})_{observed} / (\text{change in average mass})_{FSR=100\%}$$

In addition, in Vogt et. al. *Anal. Chem.* 2005, 77, 2034-42 referred to herein as Vogt (2005), the change in average mass of a peptide was calculated as the sum of change in average mass of the individual amino acids of the peptide. The techniques disclosed herein differ from that of Vogt (2003) and Vogt (2005) in that the mass shift of the $^2$H-isotopomers or $^{15}$N isotopomer distributions is determined from known parameters N and p, (parameters of a binomial distribution) using mathematical manipulation of intensities of all isotopomers from a spectrum. PSR (or FSR) is determined by comparing the observed and predicted change in the average mass (mass shift) or the observed and predicted mass isotopomer intensities. Unlike Vogt's method, a reference protein with FSR close to 100% is not required.

A mathematical algorithm which is capable of separating overlapping mass spectra of labeled and unlabeled proteins is disclosed. The algorithm may be performed by a processing system of any number of devices as disclosed herein. With the capability of separating spectrum with a minimum number of mass shifts, stable isotopes can be introduced into protein at much lower enrichment than previously used from nutrient containing $^{13}$C, $^2$H or $^{15}$N (carbon-13, deuterium and nitrogen-15) for the determination of protein synthesis/turnover in cell culture, whole animal or human experiments.

The mathematical algorithm is based on the binomial distribution of mass isotopomers when the "heavy" isotope such as $^{13}$C is used in the presence of the "light" isotope such as $^{12}$C. In a molecule consisting of carbon, nitrogen, oxygen and hydrogen, the molecular weight as well as the distribution of isotopomers can be predicted from the molecular weights of the elements as well as the frequency of finding their corresponding heavy isotopes. In general, the isotopomer distribution can be seen as a concatenation of groups of isotopomers from the same elements as follows:

[carbon isotopomers]⊕[hydrogen isotopomers]⊕[oxygen isotopomers]⊕[nitrogen isotopomers]

For the sake of discussion, we simplify the experimental model to three specific conditions:

[background $^{13}$C isotopomers]⊕[deuterium isotopomers]
[background $^{13}$C isotopomers]⊕[$^{15}$N isotopomers]
[background $^{13}$C isotopomers]⊕[$^{13}$C isotopomers]

The term "background $^{13}$C isotopomers" as used above refers to isotopomers formed from natural abundance of $^{13}$C.

Figure 8:
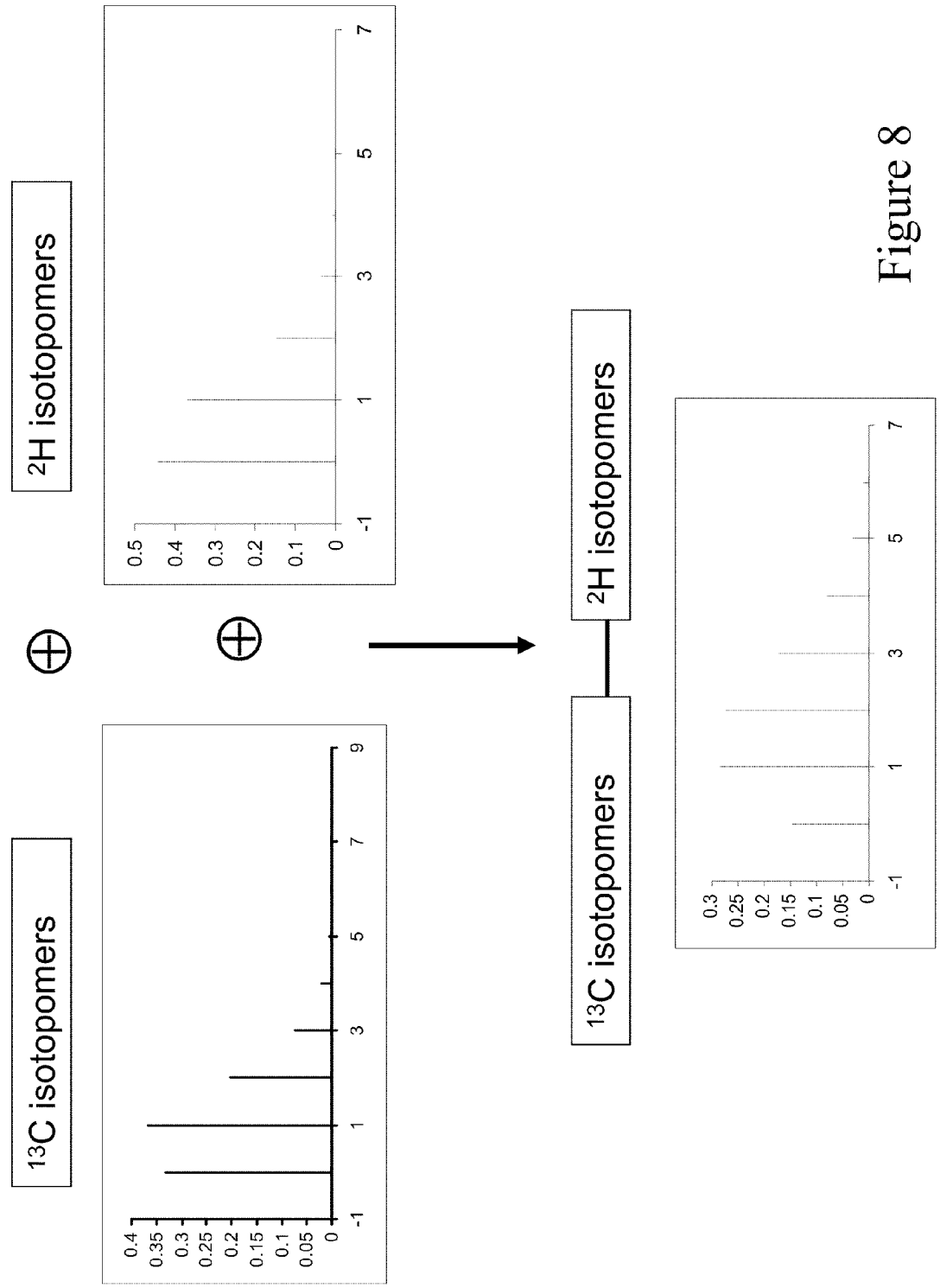
FIG. 8 shows the algorithm of isotopomer formation (concatenation operation) from two different isotopes in a newly synthesized protein.

⊕ is a special operation which generates the mass isotopomers of the whole molecules from the isotopomers of its parts. See, for example, Lee W N, et al. *Measurement of fractional lipid synthesis using deuterated water ($2H_2O$) and mass isotopomer analysis.* Am J. Physiol. 1994 March; 266(3 Pt 1):E372-83 referred to herein as Lee et al. (2004). For example, if mass isotopomer distribution in carbon in a peptide is given by the coefficients of the vector $[a_0m0, a_1m1, a_2m2, \ldots]$ and the isotopomers from deuterium incorporation by the coefficients of the vector $[b_0m0, b_1m1, b_2m2, \ldots]$, the isotopomers of the peptide is given by the coefficient of the vector $[a_0b_0m0, (a_0b_1+a_1b_0)m1, (a_1b_1+a_2b_0+b_2a_0)m2, \ldots]$. The sum of the coefficients is equal to 1 ($\Sigma a_i=1$; and $\Sigma b_i=1$). As illustrated by the example, the coefficient of the combined peptide is given by the sum of the products with subscript indices equal to the mass isotopomer number. In this case, the coefficient of m0 is given by $a_0b_0$ and m1 given by $a_0b_1+b_0a_1$. FIG. 8 shows an example of how the observed spectrum of the heavy peptide (deuterium enrichment 4%) in FIG. 7 is the result of combination of carbon mass isotopomers and deuterium isotopomers for different deuterium enrichment. When there is little overlap between the "labeled" and the "unlabeled" or background spectrum, another exemplary technique for use of the concatenation operation is illustrated in Example IV.

Figure 9:
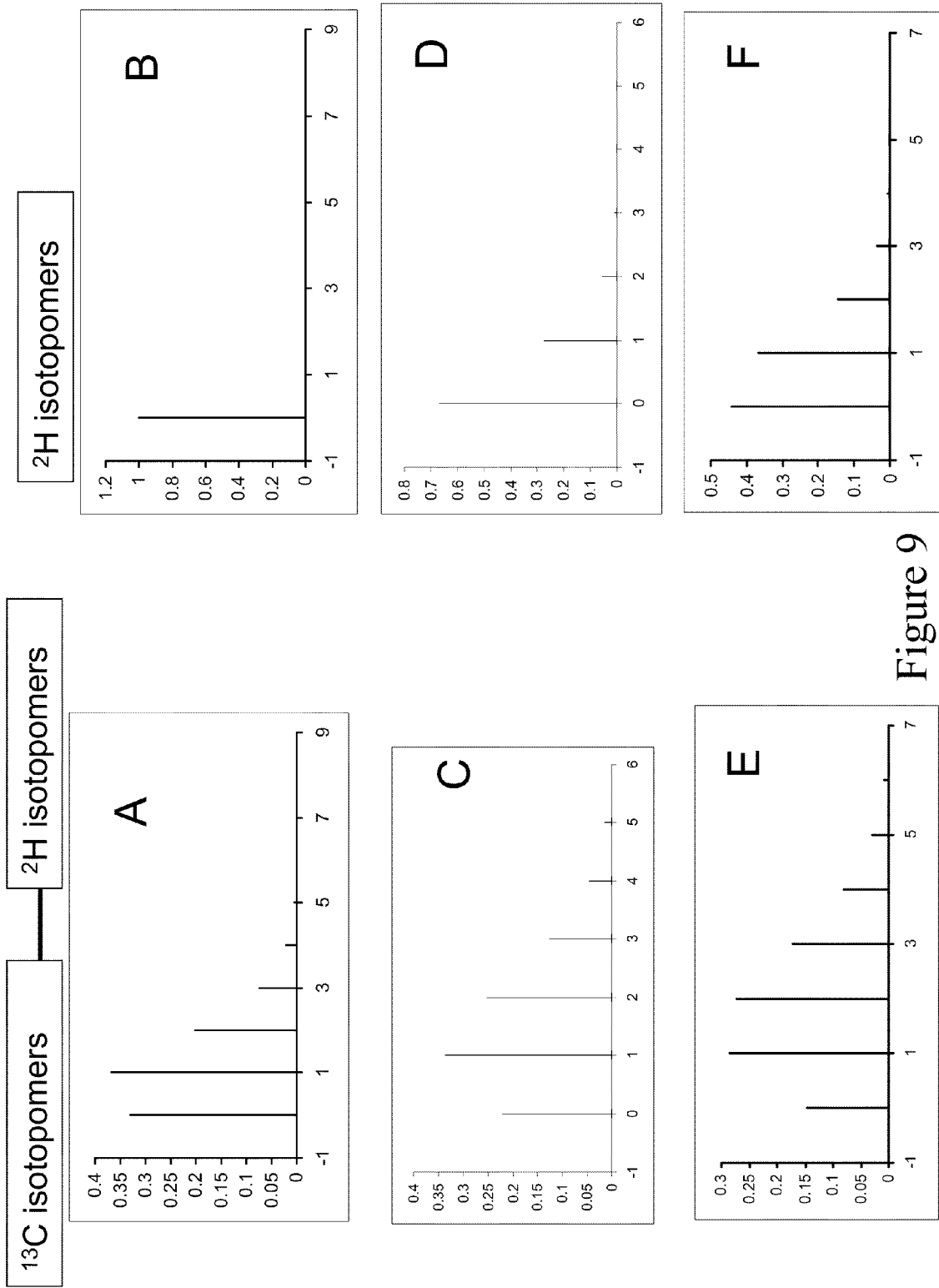
FIG. 9 illustrates the inverse of the above algorithm (inverse concatenation operation) by which deuterium isotopomer distribution can be deduced from the observed spectrum containing both $^{13}C$ and $^2H$ isotopes (background subtraction).

The mathematical algorithm described herein takes the observed spectrum and converts it back to a deuterium isotopomer spectrum using regression analysis as illustrated in FIG. 9. Since m0 of the deuterium spectrum can be from the newly synthesized peptide or the pre-existing peptide, the difference between theoretical m0 from the newly synthesized peptide and the observed m0 give the fraction of preexisting peptide. (see FIG. 10).

An experimental approach of adding a "fixed" amount of unlabeled proteins as a recovery standard to the protein extract of "control" and "treated" cells is also disclosed. The change in the "labeled"/"unlabeled" or "heavy"/"light" ratio of the same peaks after the addition of the standard can be used to determine protein expression ratio as previously described.

Figure 11:
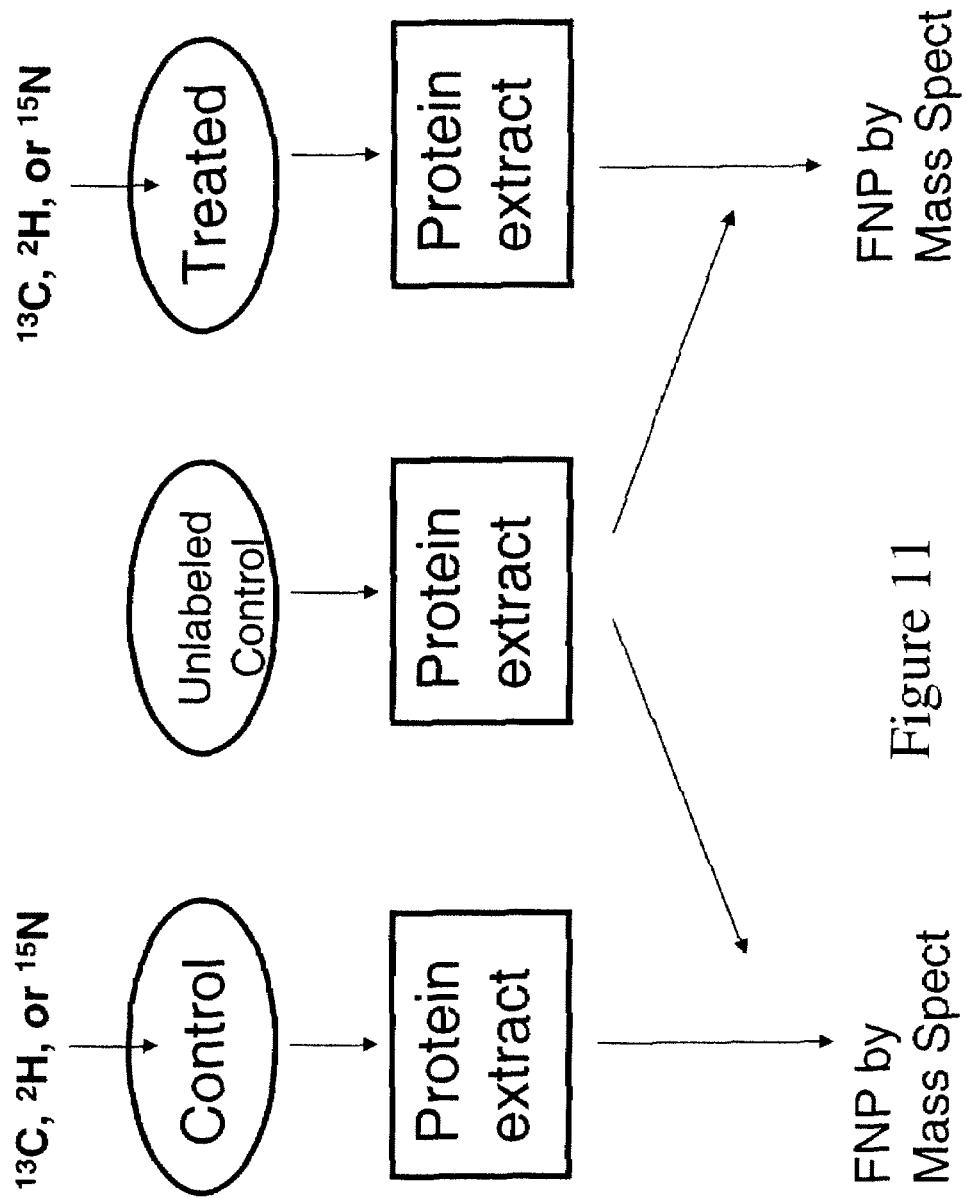
FIG. 11 is a schematic of an experimental procedure for the determination of protein expression using FNP ratios. FNP (treated) to FNP(control) gives the relative expression of the protein between treated and control.
Figure 12A:
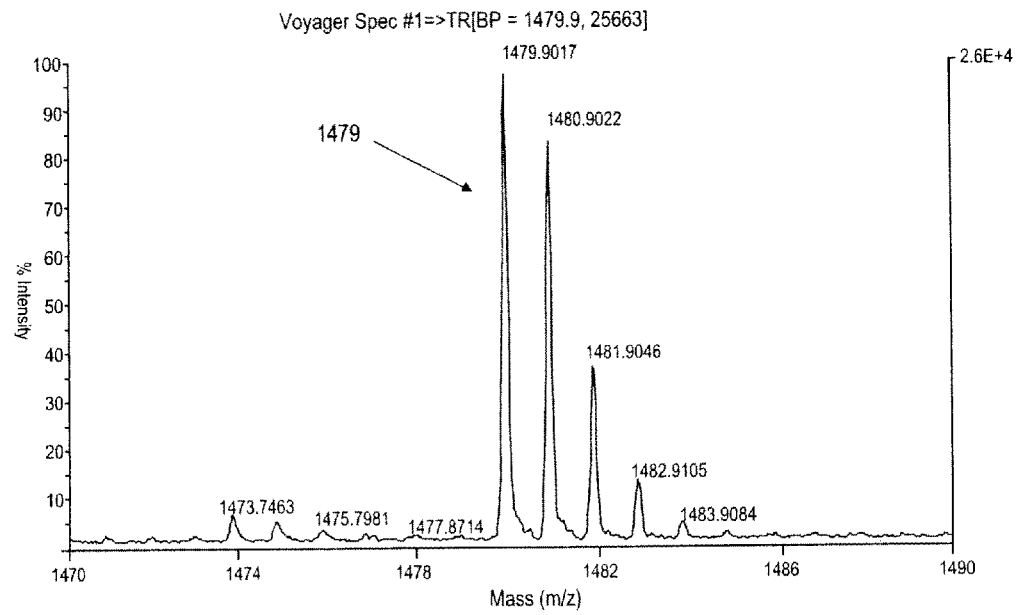
FIGS. 12A-12D show four peptides found in an albumin fraction of rat serum.
Figure 12B:
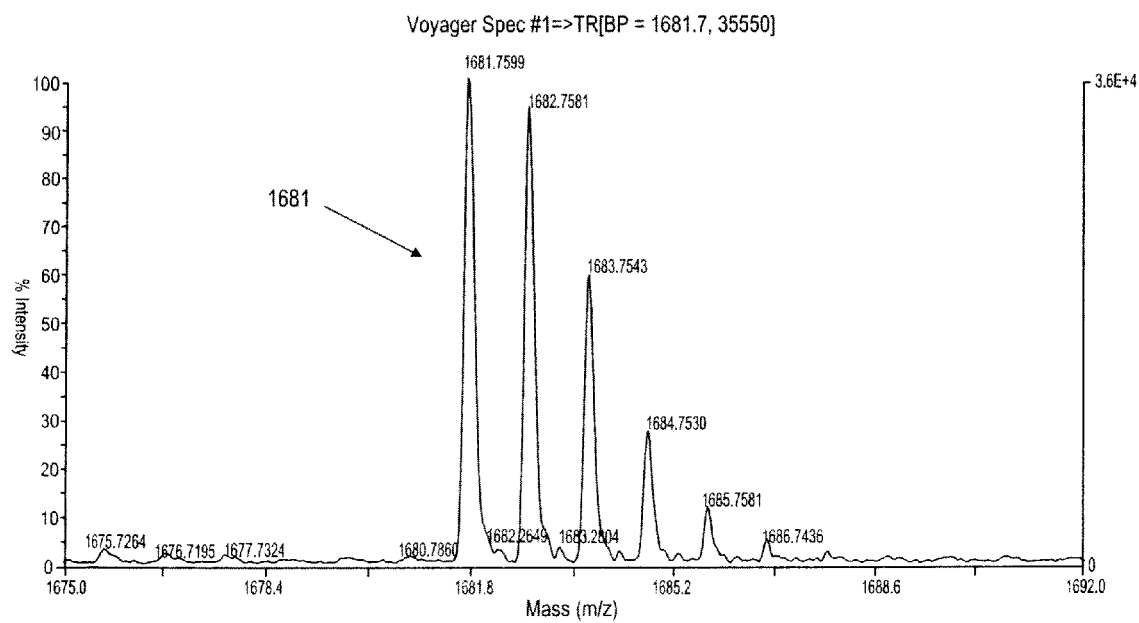
Figure 12C:
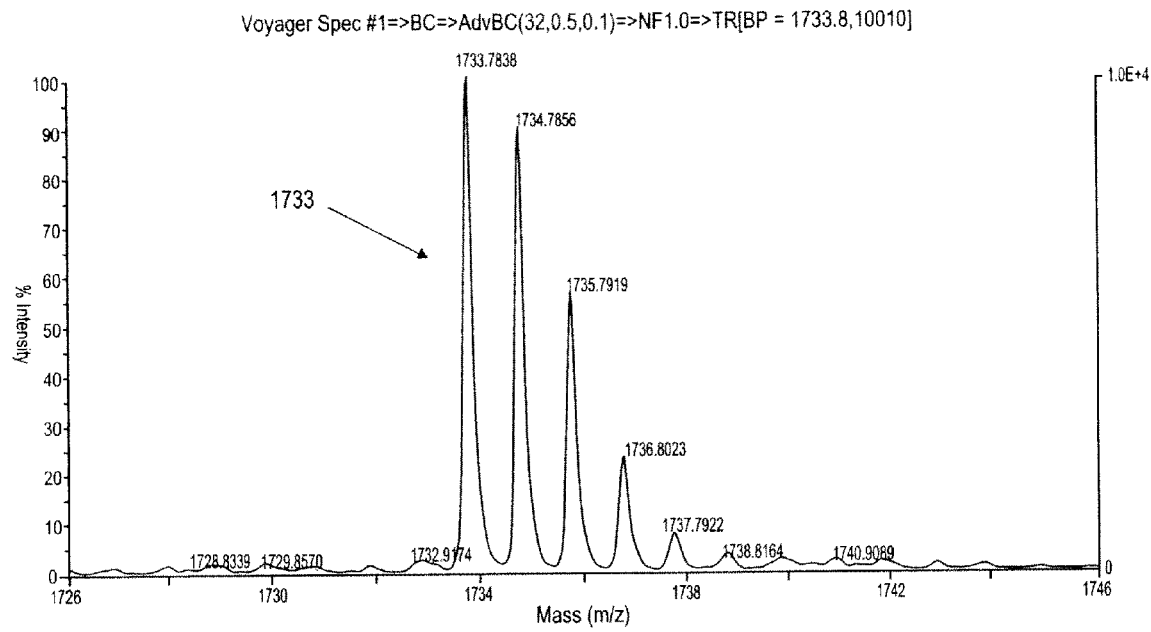
Figure 12D:
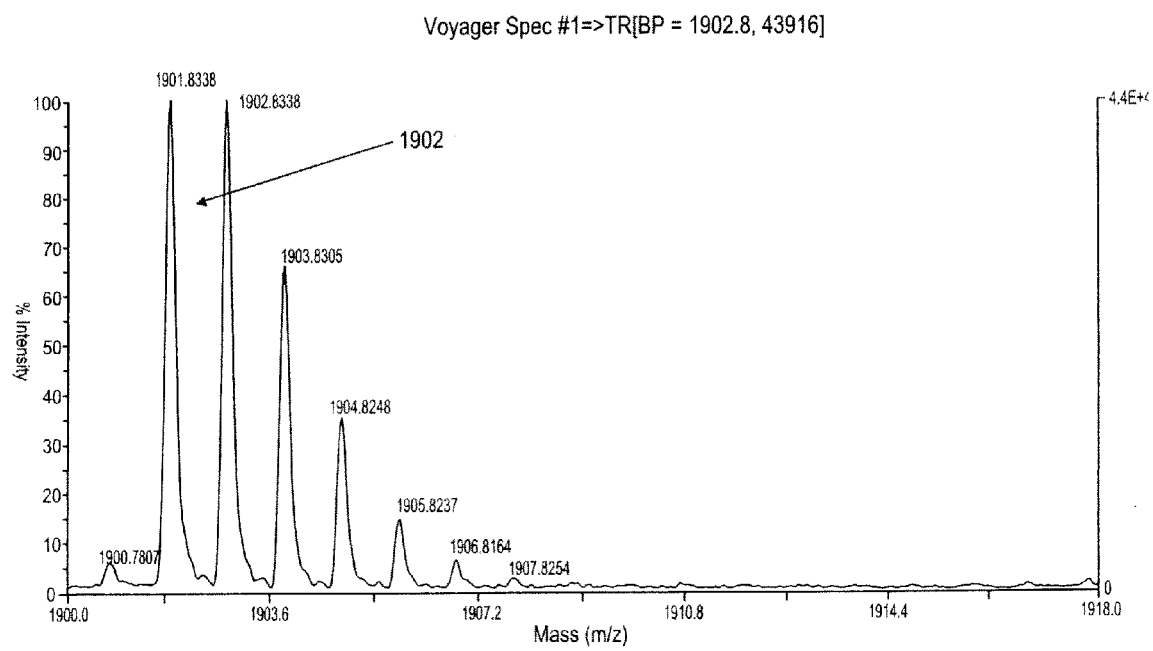
Figure 13A:
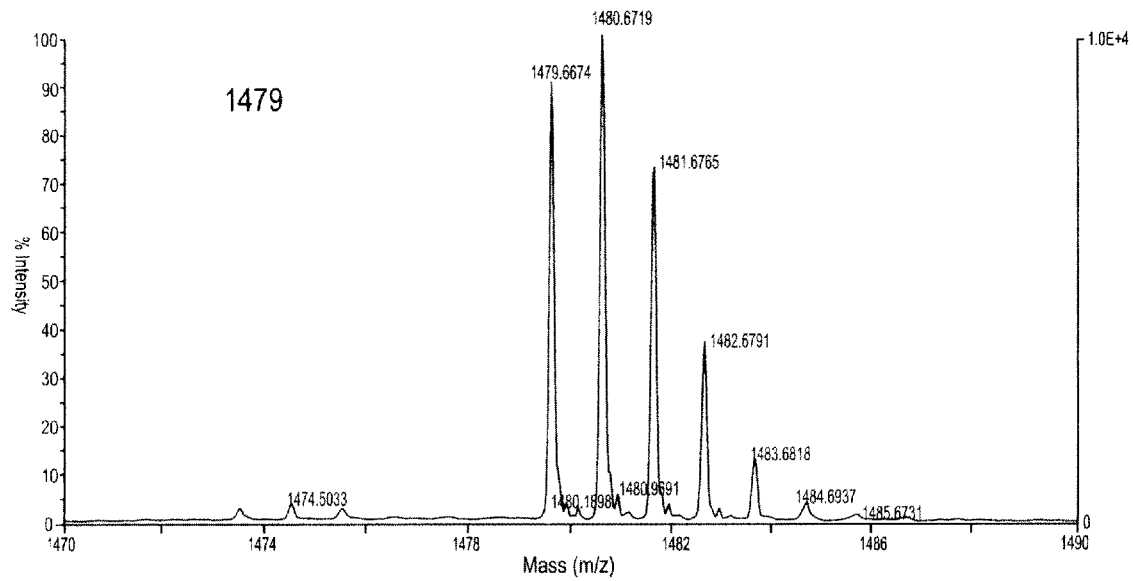
FIGS. 13A-13D show peptides found in serum of rat treated with deuterated water (2.5% enrichment) for 5 days.
Figure 13B:
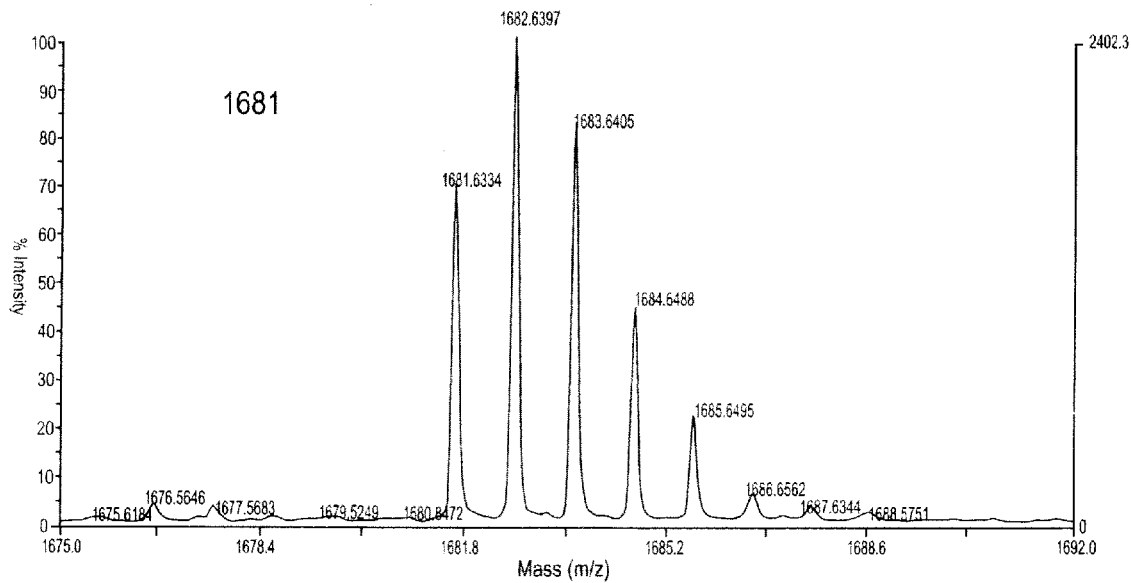
Figure 13C:
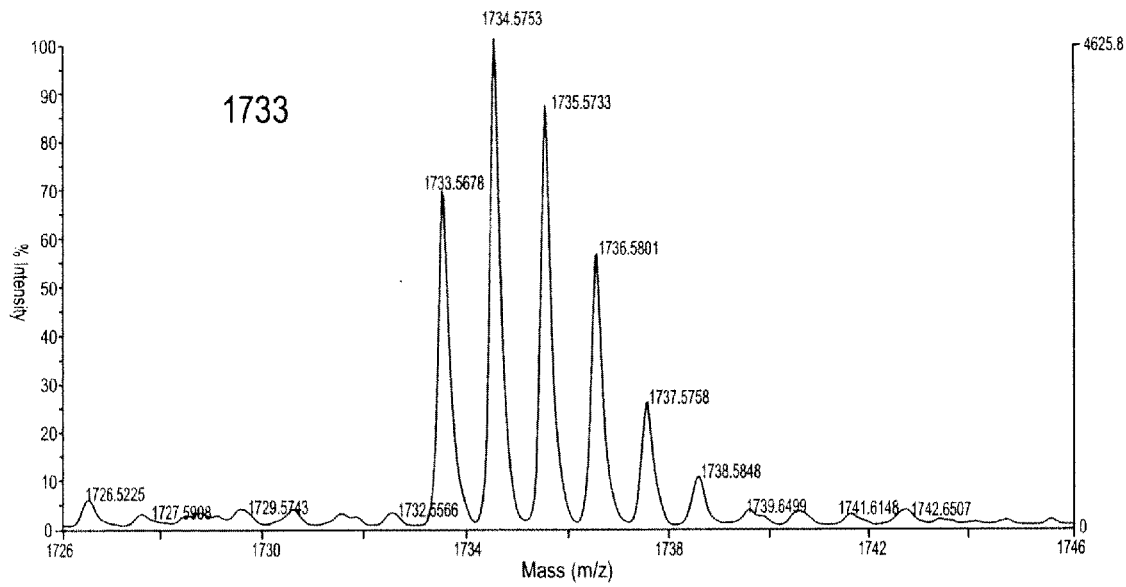
Figure 13D:
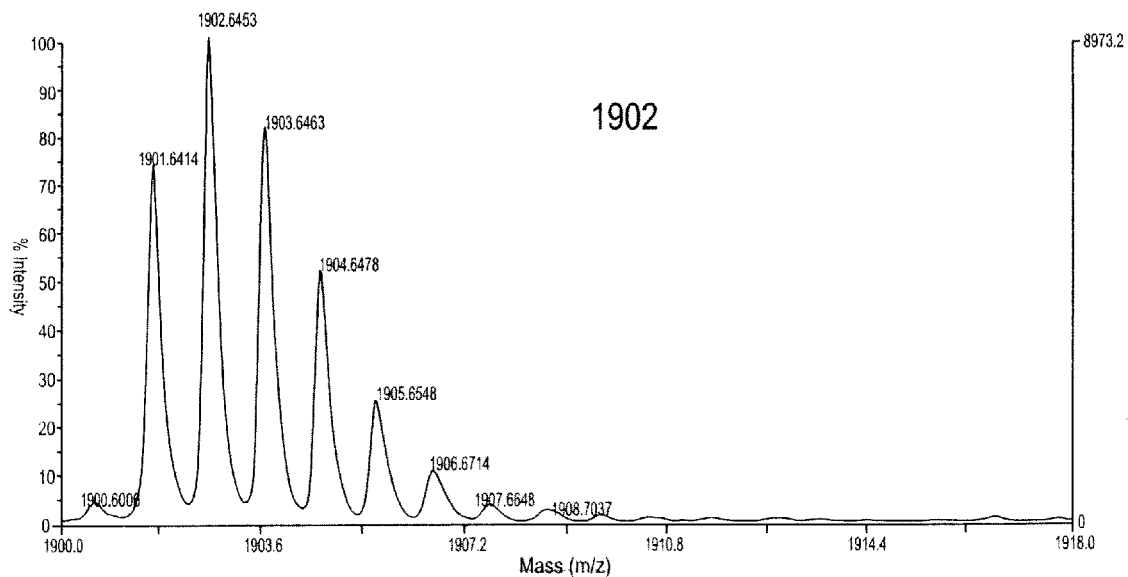

FIG. 11 is a schematic of an experimental procedure for the determination of protein expression using FNP ratios. Isotope doping is carried out in control and treated cells (animals or humans). A similar experiment is carried out in control cells (or animals or humans) without doping and the protein extract is used as a recovery standard. Using mass spectrometry data, FNP is determined on protein extracts of control and treated cells (or animals or humans) with or without the recovery standard. The effect of the added recovery standard on the FNP ratio reflects the differences in the concentration of the protein between the control and the treated cells. When the concentration of the protein of interest in one of the samples (control plus unlabeled control, treated plus unlabeled control or the unlabeled control) is known, the method can be used for quantitation of protein in either treated or untreated samples.

A technique for labeling of proteins with stable isotopes and the quantification of such labeled proteins using mass spectrometry are further disclosed. One advantage of this technique is that the dynamic relationship of proteins synthesis/turnover to cellular function can be assessed. The technique reveals information on transcriptional regulations and signaling pathways through their impact on protein synthesis/turnover. The use of randomly introduced stable isotopes $^{13}$C, $^2$H and $^{15}$N (carbon-13, deuterium and nitrogen-15) into protein is feasible and practical in both tissue culture as well as in whole animal or human settings. Such measurements allow physicians and researchers to detect changes in proteins that perform the biological functions in response to metabolic or genetic signals such as nutrients, hormones or drugs, and are of great use in the field of biomarker discovery.

In one embodiment, a uniformly $^{13}$C labeled glucose molecule, such as [U-$^{13}C_6$]-D-glucose tracer, is added to tissue culture or administered to the subject to introduce heavy isotope $^{13}$C (carbon-13) into newly synthesized proteins. The $^{13}$C labeled glucose molecule is labeled randomly such that the probability of finding a $^{13}$C in any carbon of the molecule is between 30-50%. The $^{13}$C labeled glucose molecule that may be used includes, but is not limited to, [U-$^{13}C_6$]-D-glucose, [1, 2-$^{13}C_2$] glucose, [1-$^{13}$C] glucose, [6-$^{13}$C] glucose, [1, 2-$^{13}C_2$]acetate, [1, 2, 3-$^{13}C_3$] lactate and combination and mixtures thereof.

Deuterated water ($D_2O$) is added to tissue culture or given to an animal such that enrichment in water is between approximately one and four percent to introduce heavy isotope $^2$H (deuterium) into proteins. The stable isotopes [1,2,3,4,5,6-$^2H_7$]glucose or perdeuterated fatty acids given in the appropriate amount can also be used to introduce deuterium into proteins. The deuterium labeled molecule that may be used includes deuterated water, perdeuterated glucose, perdeuterated fatty acids and combination and mixtures thereof.

$^{15}$N amino acids (individually or as a mixture) are added to tissue culture or given (fed) to an animal such that enrichment $^{15}$N in amino acids is approximately between 5 and 15 percent to introduce heavy isotope $^{15}$N(N-15) into proteins. The stable isotopes $^{15}$N ammonium chloride ($^{15}$NH$_4$Cl) can also be used to introduce N-15 into proteins in certain experimental conditions. The N-15 labeled molecule that may be used includes $^{15}$N amino acids (individually or as a mixture), $^{15}$N ammonium chloride and combination and mixtures thereof.

Proteins from cells treated with stable isotopes are extracted by commonly practiced procedures. For example, cells or tissue samples are washed twice with phosphate-buffered saline to remove serum proteins and then scraped in a lysis buffer, e.g. a buffer containing 1% SDS, 1% Nonidet P-40, 50 mM Tris, pH 7.5, 150 mM NaCl and protease inhibitors (Complete™ tablets; Roche Diagnostics, Mannheim, Germany). The lysate is sonicated for two cycles of 30 seconds each and centrifuged to pellet cellular debris.

Protein concentration in lysate is measured using the Bradford protein assay or assay by the Lowry method. To determine expression ratio, mixtures of lysates of control and treated cells are combined in a protein concentration ratio of 1:1.

The extracted proteins can further be separated/purified by sizing columns, by 2-D gel electrophoresis or by specific immuno-precipitation. Protein extract or specific protein isolate is digested by trypsin or other proteases before mass spectrometry assay. The mass isotopomer distribution in peptides can be obtained from MALDI-TOF, MALDI-TOF/TOF, linear trap such as LCQ deca or other high resolution mass spectrometers (e.g. LTQ-FT, FTICR).

The mass isotopomer distribution of the "light" peptide is used to derive the mass isotopomer distribution of the "heavy" counterpart of the peptide using multiple linear regression analysis. This procedure is the same as removing the contribution of the "light" background from the "heavy" peptide giving a distribution of isotopomers containing deuterium.

FIG. 9 illustrates the mass isotopomer distributions of an unlabeled peptide and its two "labeled" counterparts from FIG. 7 are represented as spectral peaks (panels A, C and E). After subtracting the contribution from natural abundance of $^{13}$C from peaks in A, C and E, the resultant isotopomer distributions excluding m0 are shown in panels B, D and F, representing the pure contribution from deuterium incorporation. The x-axis is in dalton mass shift from the monoisotopic species (m0). The scale of the axis is in integer increments (1, 2, 3, etc.). The y-axis represents a molar fraction. Using the consecutive isotopomer ratio method, the product of the number of deuterium substitution and the deuterium enrichment (Np) can be estimated as described in Lee W N, et al. *Measurement of fractional lipid synthesis using deuterated water ($H_2O$) and mass isotopomer analysis*. Am J. Physiol. 1994 March; 266(3 Pt 1):E372-83.

When there is no deuterium incorporation, the isotopomer fraction of the monoisotopic peptide is 1 (FIG. 9, Panel B).

The observed mass isotopomer distribution in a peptide from the protein extract is a linear combination of the mass isotopomers of the "light" species and those of the "heavy" species. Once the mass isotopomer distribution of the "light" and the "heavy" species of the peptide are known, the contribution of the "heavy" peptide to the total mass isotopomer distribution is new protein fraction (FNP) of the peptide and the protein from which it is derived.

Figure 10:
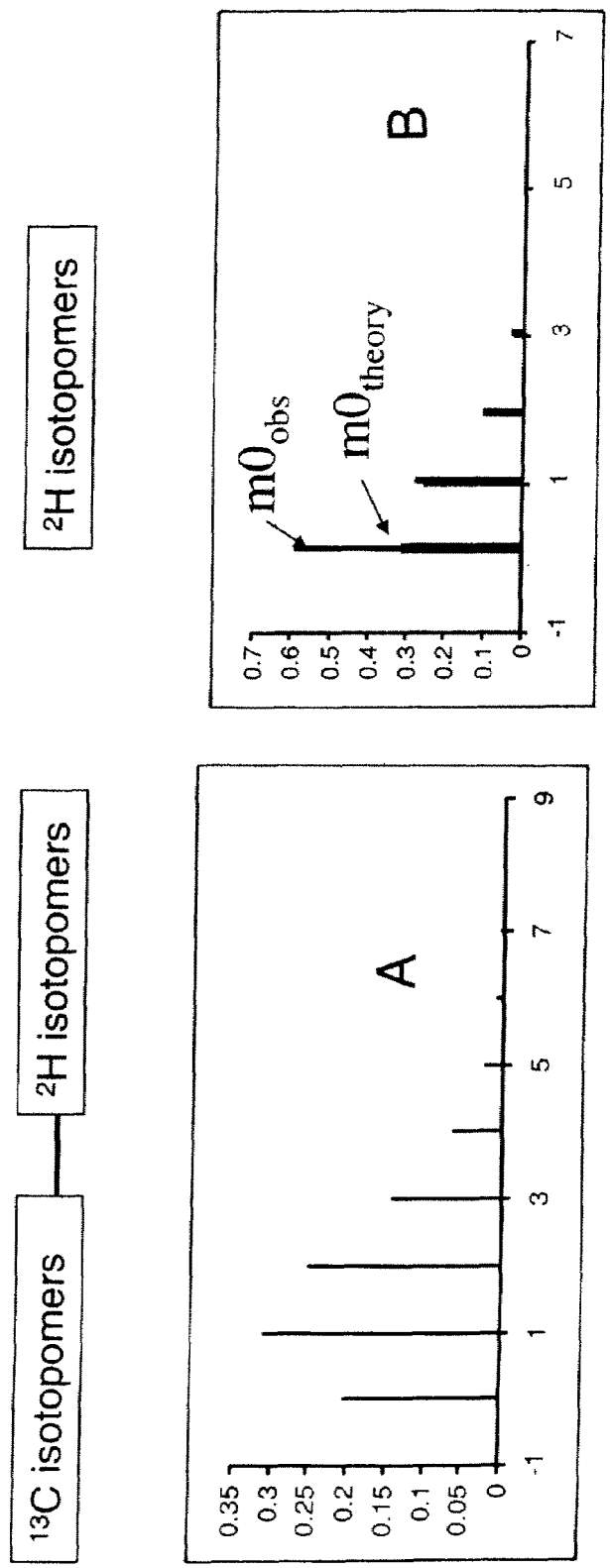
FIG. 10 illustrates the application of the algorithm of FIG. 9 to estimate newly synthesized protein fraction.

FIG. 10 illustrates an estimation of a newly synthesized protein fraction. The observed isotopomer distribution is represented by the curve of data series 3, which is the result of linear combination of 30% "light" (Series 1 of FIG. 7) and 70% "heavy" peptide (series 3 of FIG. 7). Panel B shows the mass isotopomer distribution of a mixture of "light" (preexisting) and "heavy" (newly synthesized) peptides. The x-axis is in dalton mass shift from the monoisotopic species (m0). The scale of the axis is in integer increments (1, 2, 3, etc.). The y-axis represents a molar fraction. Using the distribution of isotopomers of the "light" peptide of FIG. 9, the deuterium isotopomer distribution is derived using regression analysis. The consecutive mass isotopomer ratio of m2/m1 or m3/m2 can be used to calculate number of exchangeable hydrogen and deuterium enrichment (Np). The isotopomer distribution of the "heavy" or "labeled" peptide is constructed based on the information of Np shown by the thicker line sections of the spectral peaks in Panel B. The FNP is the fraction of isotopomers in the mixture contributed by the "heavy" peptide. Alternatively, the pre-existing fraction is given by 1 minus the sum of the labeled fraction, from which the fraction of new synthesis can be determined, shown as the thinner line sections of m0 in Panel B. The section labeled as "m0 obs" represents the fraction of molecules without containing any deuterium. The section labeled as "m0 theory" represents the fraction of molecules without deuterium as expected from the theoretical binomial distribution for the given N and p.

The amino acid sequence of peptide can be identified using post source decay fragmentation micro-sequencing techniques of MS/MS such as Sequest of LCQ decay or LTQ-FT.

The determination of FNP can be repeated at multiple time intervals after the introduction of the stable isotope. The FNP is expressed as a function of time and the turnover rate as well as half-life of the protein can be calculated as previously discussed.

Figure 1:
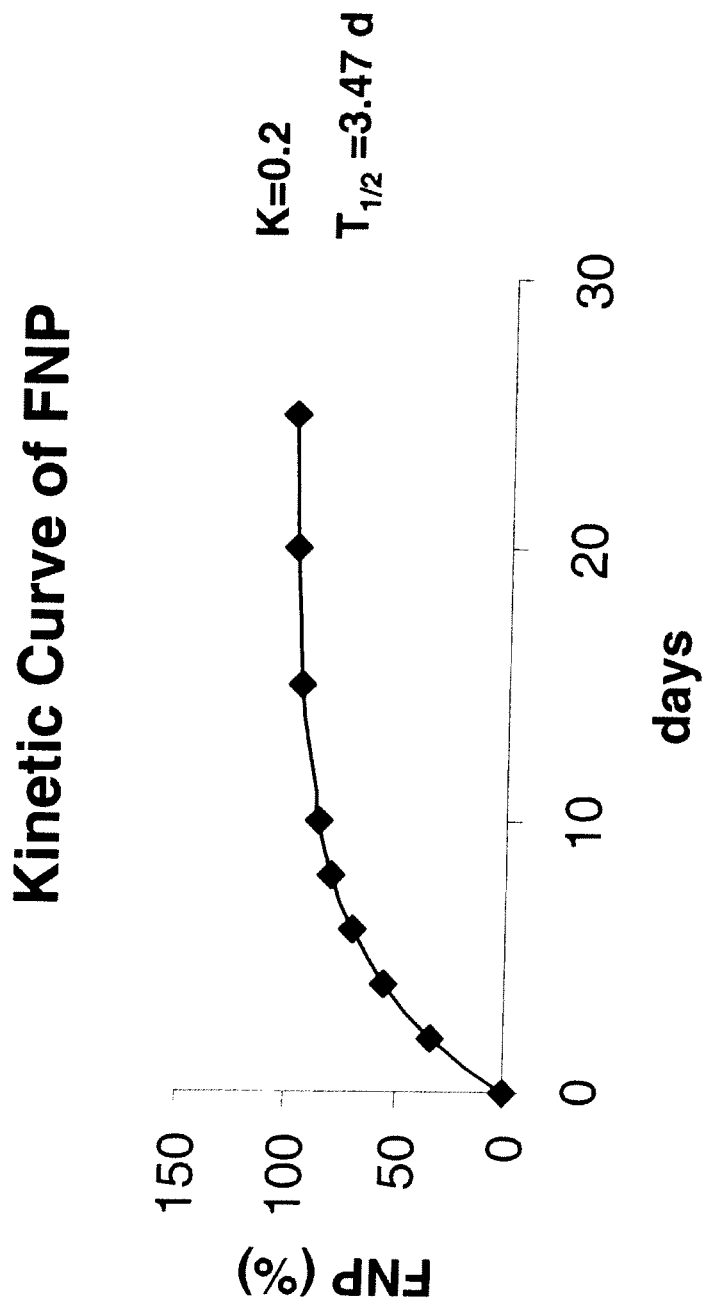
FIG. 1 shows the relationship between the fraction of new protein and protein turnover in a one-compartment model.
Figure 2:
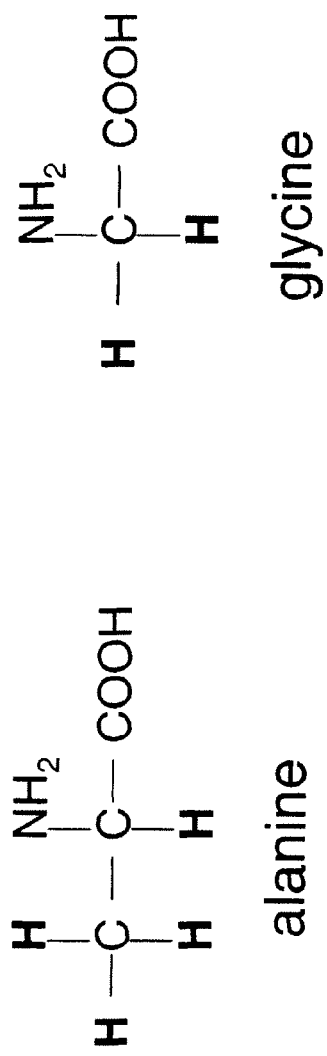
FIG. 2 shows the incorporation of deuterium or nitrogen into non-essential amino acids (NEAA) through transamination.
Figure 2:
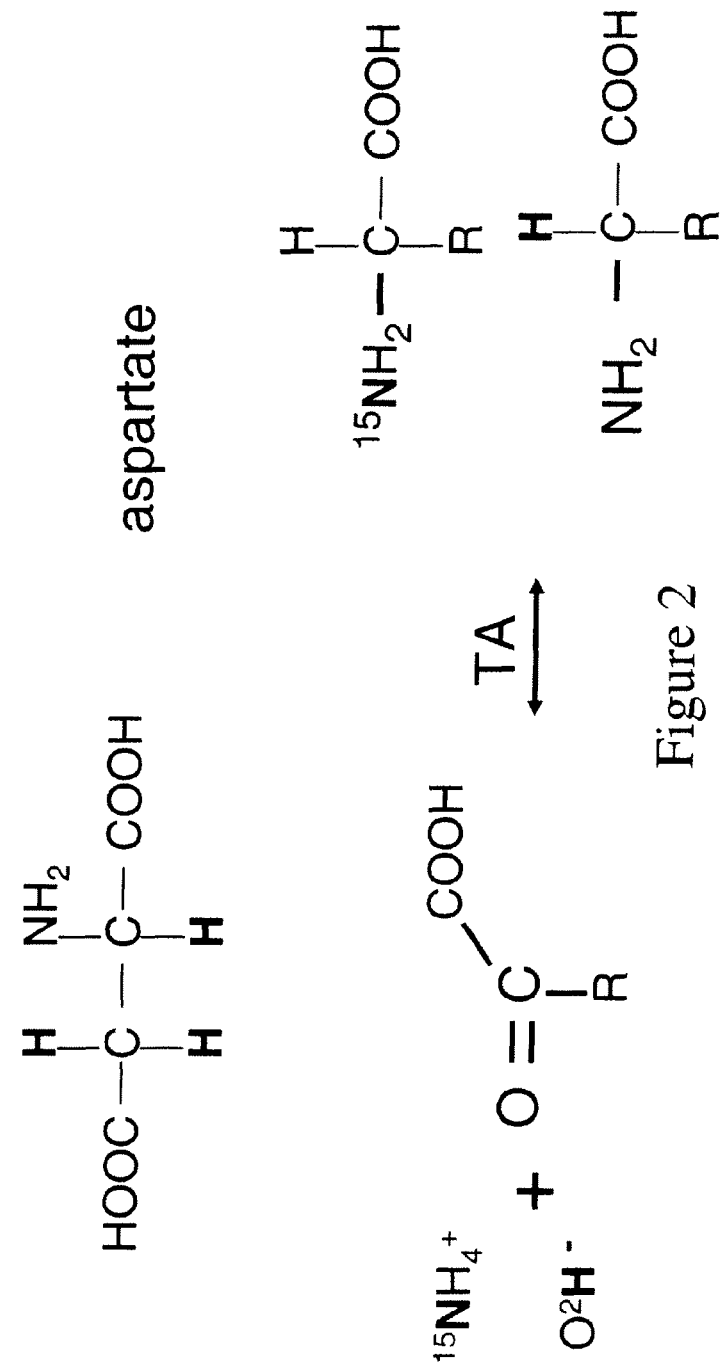
Figure 3:
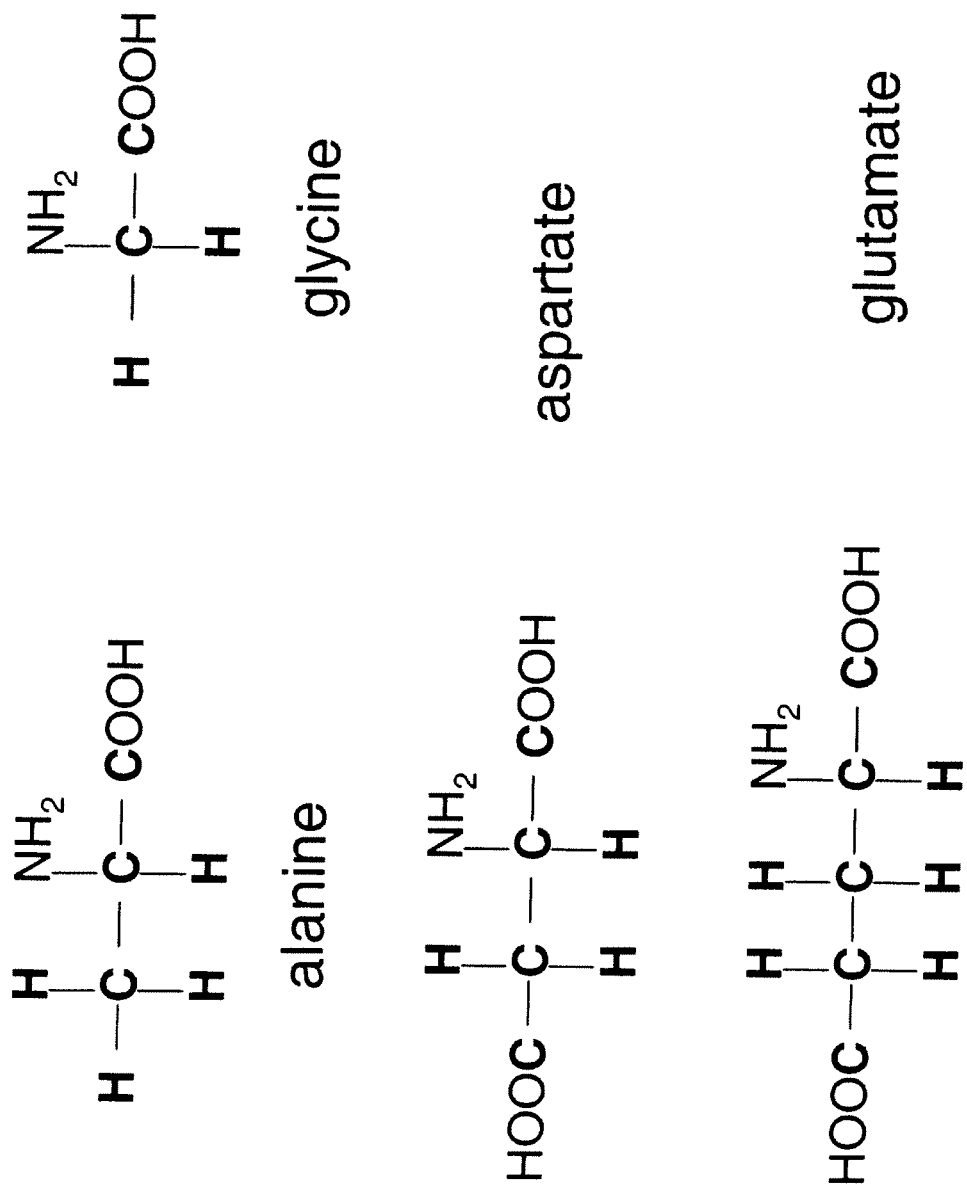
FIG. 3 shows the incorporation of $^{13}C$ into amino acids from $[U^{13}C_6]$-glucose.
Figure 4:
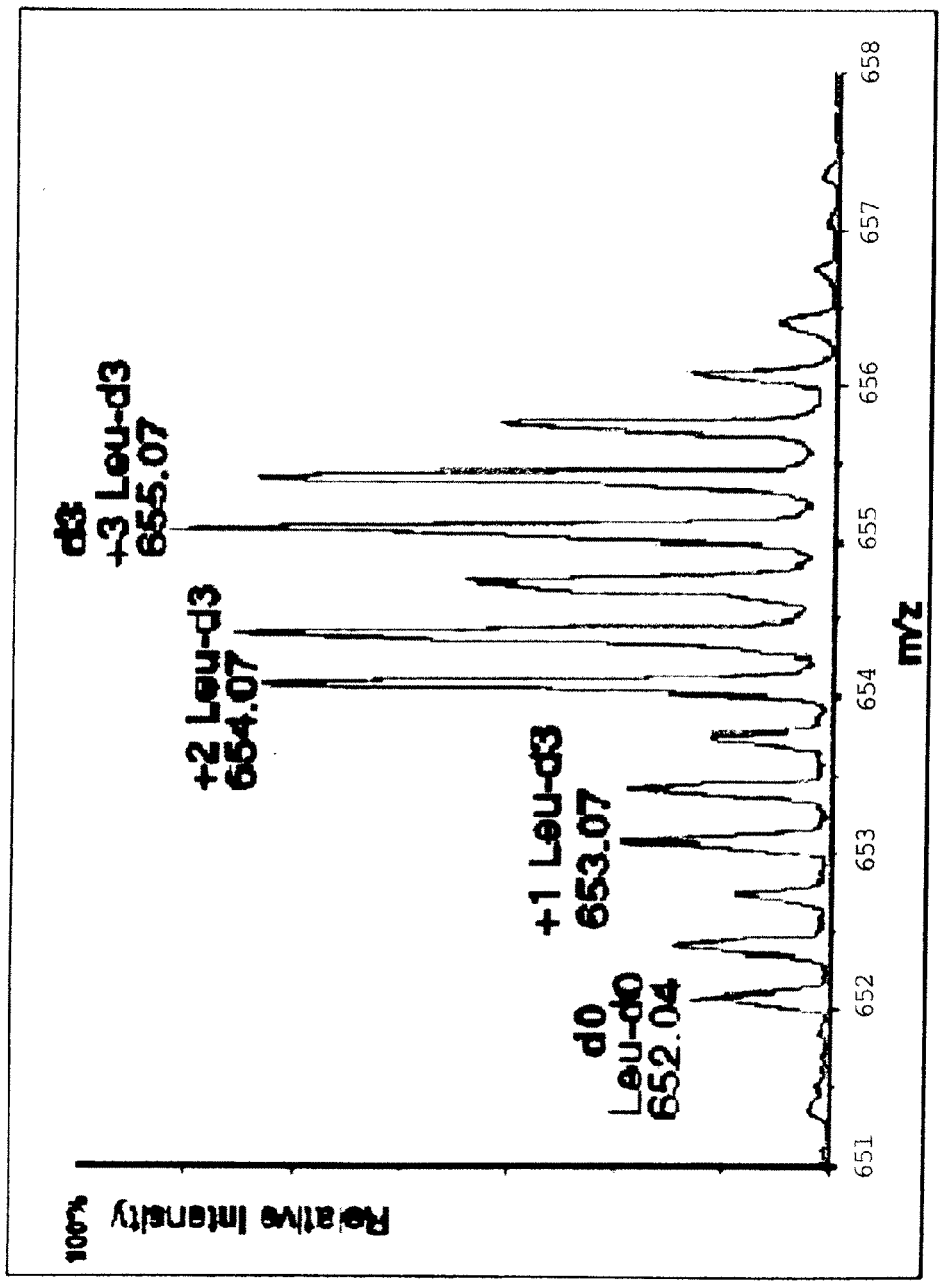
FIG. 4 shows peptide spectrum of a peptide with 3 positive charges containing three leucines resulting from the incorporation of d3-leucine. Multiple peaks (leu-d0, +1 leu-d3, +2 leu-d3 and +3 leu-d3) arise from the incorporation of different number of d3-leucine.
Figure 5:
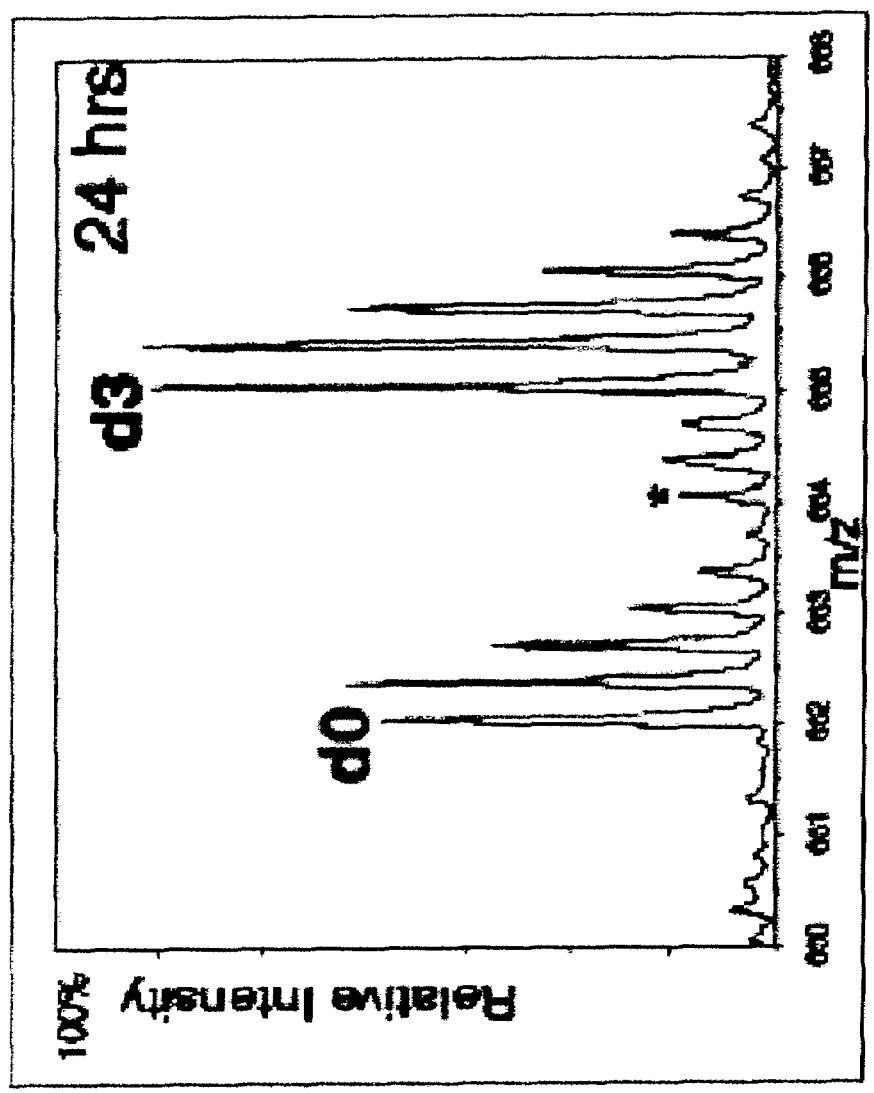
FIG. 5 shows mass shifts in the same peptide as in FIG. 4 containing only d3-leucine (+3 leu-d3) after incubation of cells in dialysed medium containing 100% d3-leucine. The spectrum was obtained using mixture of labeled (+3 leu-d3 or d3) and unlabeled (leu-d0 or d0) peptide.
Figure 6:
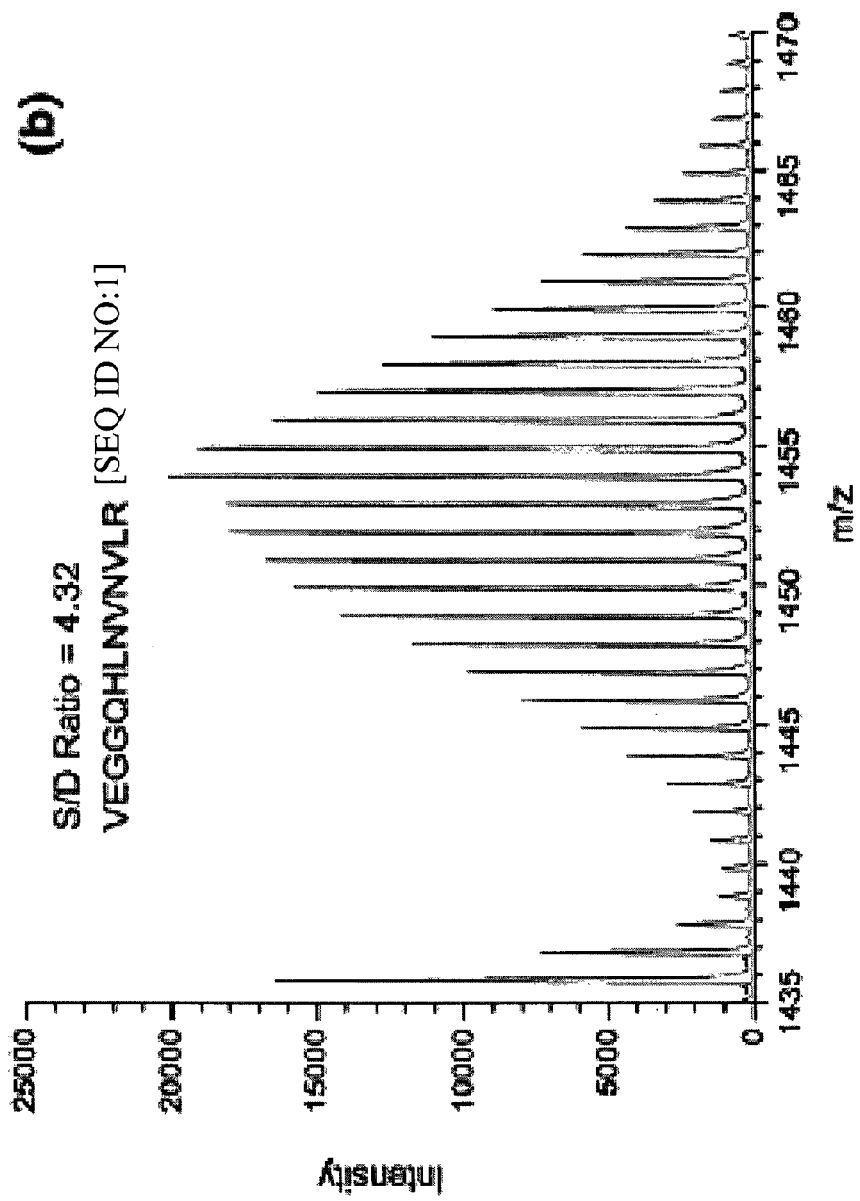
FIG. 6 shows the labeling of protein with highly enriched (>95%) $[U^{13}C_6]$glucose. The ratio of labeled to unlabeled peptide is 4.32 to 1.

FIG. 1 shows the relationship between the fraction of new protein and protein turnover. The fraction of new protein increases over time according to a single compartment model. $FNP(t)=1-FNP(max) \times e^{-kt}$, where k is the fraction that is cleared (turned over) per unit time. From k, $t_{1/2}$ can be calculated. With sufficient sampling points, more complex models can be supported.

FIG. 8 shows isotopomer formation in a newly synthesized protein. The mass spectrum of FIG. 8 is shown in a centroid mode (i.e. as the intensity over a certain integer mass). The top left panel shows the isotopomers of a peptide containing 100 carbon atoms having an average enrichment of 1.1% $^{13}$C (a hypothetical polymer of 100 carbon atoms enriched with 1.1% $^{13}$C). The distribution gives what is commonly known as the "isotope envelop". The top right panel shows the isotopomer distribution of an equivalent of a "20-mer" of hydrogen having 2.5% deuterium (a hypothetical polymer of 20 hydrogen atoms enriched with 2.5% deuterium). Using the operation previously described, the observed isotopomer distribution is shown at the bottom panel, which is essentially the distribution of top right panel with a +1 mass shift. The x-axis is in dalton mass shift from the monoisotopic species (m0). The scale of the axis is in integer increments (1, 2, 3, etc.). The y-axis represents a molar fraction.

When cells or animals are exposed to therapeutic intervention with drugs, hormones or chemicals, profiles of protein synthesis and relative protein expression between the "treated" and "untreated" samples can be determined as previously described and illustrated in FIG. 8. For example, if 15 mg of protein X is recovered in the "treated" sample and the new fraction (FNP) is 0.3333; and 25 mg of protein X is recovered from the control or "untreated" sample and its new fraction is 0.20. After the addition of 5 mg of "light" or "unlabeled" protein X to each of the sample as a recovery standard, the new fraction of the treated sample becomes 0.25 and the new fraction of the control becomes 0.1667. The ratio of these new FNP's (0.1667/0.25) gives a relative expression ratio of 0.6667, which accurately reflect the relative concentration in these samples (15/25) before the addition of the recovery standard.

In some embodiments, a molecule which contains one of the stable isotopes ($^{13}C$, $^{2}H$ or $^{15}N$), is added to tissue culture medium, or infused into (or fed to) a living organism (e.g. animal or human) at the prescribed dose. The molecule may incorporate itself into proteins that are actively synthesized. Those proteins are collectively referred to here as a proteome. The method described can be applied to all such proteins of the proteome providing a profile of protein synthesis rate as well as relative protein expression.

Variations and changes in components of the proteome is the result of changes in individual protein synthesis and degradation, and reflect the adaptation of an organism to its microenvironment, as defined by substrate availability and hormonal milieu, through altered gene expression and through the activation of signaling cascades. The major regulatory components of cell function, the genome, transcriptome and substrate availability ultimately act on the proteome resulting in the expression of a specific phenotype. By using a high throughput method to survey the protein synthesis and expression of proteins in a cell within an organism it is possible to establish information with respect to functional genomics and proteomics critical to cellular function.

The following examples are illustrative, but not limiting, of the methods and compositions described. Other suitable modifications and adaptations of the variety of conditions and parameters normally encountered in therapy are within the spirit and scope of the embodiments.

EXAMPLE I

Illustration of Concatenation Operation ($\oplus$) and its Inverse ($\varnothing$) Operation on Mass Isotopomer Distribution In a molecule that contains more than one element containing isotope species, the molecular spectrum can be considered as a complex mixture of its components. For example, the distribution of molecules affected by $^{13}C$ natural abundance is approximated by a binomial distribution with N(c) being the number of carbon and p(c) being the natural enrichment (1.1%). This distribution is reflected in the isotopomer distribution reflected in the "isotope envelop". In a protein that is synthesized in the presence of deuterium (e.g., 4.0% deuterated water), when the contribution of other isotopes is ignored, the distribution of molecules having 0, 1, 2, 3 . . . deuterium substitutions is given by the binomial distribution with N(d) being the number of possible deuterium substitution and p(d) the deuterium enrichment in water. The isotomoper distribution in these components are designated as (C-isotopomers) and (d-isotopomers). The protein spectrum can be considered as the weighted sum of a series of spectra having 0, 1, 2, 3, . . . deuterium substitutions, which can be derived from (C-isotopomers) and (d-isotopomers) using the concatenation operation ($\oplus$).

(C-isotopomers)$\oplus$(d-isotopomers)=observed mass isotopomers in protein.

If distribution of isotopomer in (C-isotopomers) is represented by the coefficients of the vector ($a_0 m0$, $a_1 m1$, $a_2 m2$, . . . ) and distribution of isotopomer in (d-isotopomers) by the coefficients of the vector ($b_0 m0$, $b_1 m1$, $b_2 m2$, . . . ). The distribution in the protein or peptide is given by the coefficients of the vector ($a_0 b_0 m0$, ($a_0 b_1 + a_1 b_0$)m1, ($a_0 b_2 + a_1 b_1 + a_2 b_0$)m2, . . . ). M0 represents the monoisotopic species and m1, m2, m3 etc. are the isotopomers containing 1, 2, 3, . . . $^{13}C$ or $^{2}H$ isotopes. The use of mi notation allows the comparison of peptide peaks of different masses.

(C-isotopomers) distribution is given by ($a_0$, $a_1$, $a_2$, $a_3$, . . . )
(d-isotopomer) distribution is given by ($b_0$, $b_1$, $b_2$, $b_3$, . . . )
isotopomers of the protein is given by ($c_0$, $c_1$, $c_2$, $c_3$, . . . )
($a_0$, $a_1$, $a_2$, $a_3$, . . . )$\oplus$($b_0$, $b_1$, $b_2$, $b_3$, . . . )=($c_0$, $c_1$, $c_2$, $c_3$, . . . )

The concatenation operation is defined by the matrix multiplication below. The c-isotopomers are arranged in a (n+1 by m+1) matrix and the d-isotopomers by a (m+1 by 1) column vector. The product is the c-isotopomers in the form of a (n+1 by 1) column vector.

$$\begin{vmatrix} a_0 & 0 & 0 & 0 & 0 & \ldots & 0 \\ a_1 & a_0 & 0 & 0 & 0 & \ldots & 0 \\ a_2 & a_1 & a_0 & 0 & 0 & \ldots & 0 \\ a_3 & a_2 & a_1 & a_0 & 0 & \ldots & 0 \\ a_4 & a_3 & a_2 & a_1 & a_0 & \ldots & 0 \\ & & & \vdots & & & \\ a_n & a_{n-1} & a_{n-2} & & \ldots & & a_0 \end{vmatrix} \begin{vmatrix} b_0 \\ b_1 \\ b_2 \\ b_3 \\ b_4 \\ \vdots \\ b_m \end{vmatrix} = \begin{vmatrix} c_0 \\ c_1 \\ c_2 \\ c_3 \\ c_4 \\ \vdots \\ c_n \end{vmatrix}$$

If the number of c-isotopomer is given by x, the number of c-isotopomers (x) is less than or equal to the number of observed isotopomers in the spectrum (n>x and n>m). The value of $a_i$ is 0 for n>i.

For a mass isotopomer distribution $c_i$ with i=n, the first matrix has the dimension of (n+1 by m+1) of the c-isotopomers and the second matrix is a column matrix (m+1 by 1) of the d-isotopomers. Many of the elements of these matrices may be zero as discussed above. The resultant (c-isotopomers) distribution is the product of these two matrices. Thus, $c_0 = a_0 b_0$
$c_1 = a_0 b_1 + a_1 b_0$
$c_2 = a_0 b_2 + a_1 b_1 + a_2 b_0$
$c_3 = a_0 b_3 + a_1 b_2 + a_2 b_1 + a_3 b_0$
etc.

The inverse operation 0 of the concatenation operation is the inverse of the above algorithm which is to determine the d-isotopomer distribution given column matrix of observed-isotopomers and square matrix of the c-isotopomers.

($c_0$, $c_1$, $c_2$, $c_3$, . . . )$\varnothing$($a_0$, $a_1$, $a_2$, $a_3$, . . . )=($b_0$, $b_1$, $b_2$, $b_3$, . . . )

It is clear by inspection that d-isotopomer distribution can be determined using multiple linear regression analysis. The coefficients obtained from linear multiple regression analysis is the deuterium isotopomer distribution ($b_0$, $b_1$, $b_2$, $b_3$, . . . ).

Using a binomial distribution with 100 carbons and $^{13}C$ enrichment of 0.011, the (C-isotopmer distribution) generated for a peptide is (0.3308, 0.3680, 0.2026, 0.0736, 0.0199, 0.0042). This is the isotope envelop below deuterium incorporation. Similarly, using a binomial distribution with 20 possible deuterium positions and deuterium enrichment of 0.04, the (d-isotopmer distribution) generated for a peptide is (0.4420, 0.3683, 0.1458, 0.0364, 0.0065, 0.0009). The isotopomers in the "isotope envelop" of the full peptide after deuterium incorporation is (0.1462, 0.2845, 0.2733, 0.1729, 0.0810, 0.0300).

The proper deuterium enrichment to be used in any experiment can be optimized using the concatenation operation. It can be shown that the inverse operation on the isotopomers in the "isotope envelop" of the full peptide and the pre-labeling peptide (C-isotopomers) gives the (d-isotopmer distribution), which shows the effect of deuterium incorporation alone. Because of the low enrichment of deuterium used in animal studies, there is a good likelihood that the newly synthesized peptide does not have any deuterium incorporation. In such experiments, m0 represents pre-existing and newly synthesized peptide. However, the fractions represented by m1 and m2 are the results of deuterium incorporation. Thus, using the consecutive mass isotopomer equation we can determine the N(d) and p(d), using the equation $m2/m1=(N-1)/2 \times p/q$ where $q=1-p$. After determining deuterium enrichment, we can estimate N(d) and fraction of newly synthesized protein by dividing the observed m1 by the theoretical m1.

EXAMPLE II

In Vivo Labeling of Plasma Proteins and the Determination of New Fractions of Labeled Proteins The following description describes the experimental steps in the calculation of the newly synthesized fraction after deuterium incorporation.

Serum was collected from a Sprague Dawley rat after eight days of deuterated water treatment. Albumin fraction was purified by AffiGelBlue® affinity column. After tryptic digest, the sample was analyzed by MALDI-TOF for peptides in the range of 1000-2000 daltons. FIGS. 12A-12D show four peptides found in an albumin fraction of rat serum. FIGS. 13A-13D show the corresponding peptides found in serum of rat treated with deuterated water (2.5% enrichment) for 5 days. The incorporation of deuterium into these peptides increases the average molecular weights and changes the appearance of the isotope envelops.

Five peptides were identified using MALDI-TOF and post-source decay analysis.

Their sequences were matched to rat serum albumin, AMP deaminase and alpha 2u-globulin as shown in Table 1 below.

TABLE 1

Peptides identified with MALDI TOF PSD

| m/z | Sequences | Protein Identity |
|---|---|---|
| 1299.4 | HPDYSVSLLLR [SEQ ID NO: 2] | Rat serum albumin |
| 1393.4 | MPLFKLTEIDDAM [SEQ ID NO: 3] | Rat AMP deaminase |
| 1479.5 | LGEYGFQNAILVR [SEQ ID NO: 4] | Rat serum albumin |
| 1609.4 | DVFLGTFLYEYSR [SEQ ID NO: 5] | Rat serum albumin |
| 1681.7 | IEENGSMR [SEQ ID NO: 6] | Rat alpha2 u-globulin |

Tryptic digest of rat albumin was identified using post-source decay (PSD) matrix-assisted laser desorption/ionization (MALDI) time-of-flight mass spectrometry.

The corresponding normalized spectra of these peaks from the sample before deuterated water treatment (unlabeled spectra) are shown in Table 2. Average mass was calculated using the method disclosed in Blom K F. *Average mass approach to the isotopic analyses of compounds exhibiting significant interfering ions.* Anal. Chem. 60, 966-971, 1988 referred to herein as Blom.

TABLE 2

Mass isotopomer distributions of the identified peptides before deuterium labeling (unlabeled peptides).

|  | m/z 1299 | m/z 1393 | m/z 1479 | m/z 1609 | m/z 1681 |
|---|---|---|---|---|---|
| M0 | 0.4892 ± 0.0038 | 0.4466 ± 0.0101 | 0.4239 ± 0.0029 | 0.3802 ± 0.0016 | 0.3307 |
| M1 | 0.3418 ± 0.0074 | 0.3393 ± 0.0047 | 0.3349 ± 0.0056 | 0.3343 ± 0.0022 | 0.3120 |
| M2 | 0.1250 ± 0.0089 | 0.1448 ± 0.0024 | 0.1480 ± 0.0030 | 0.1807 ± 0.0034 | 0.1880 |
| M3 | 0.0368 ± 0.0010 | 0.0474 ± 0.0110 | 0.0581 ± 0.0056 | 0.0724 ± 0.0010 | 0.0913 |
| M4 | 0.0060 ± 0.0039 | 0.0127 ± 0.0044 | 0.0247 ± 0.0025 | 0.0217 ± 0.0017 | 0.0430 |
| M5 | 0.0007 ± 0.0004 | 0.0051 ± 0.0025 | 0.0105 ± 0.0038 | 0.0106 ± 0.0023 | 0.0156 |
| Average Mass | 1300.1348 | 1394.2474 | 1479.4711 | 1610.4081 | 1682.8889 |

The averages and standard deviations were calculated from triplicate MADI-TOF analyses. There was only one analysis for the peak at m/z 1681. Average mass was calculated according to Blom.

The deuterium enrichment in water is estimated to be 2.5% using deuterium incorporation into palmitate. Using results of m/z 1393 in Tables 1 and 2, the algorithm for the determination of deuterium isotopomers of the protein was set up using the inverse concatenation operation.

The regression matrices of the concatenation operation previously discussed are shown below.

$$\begin{vmatrix} 0.4466 & 0.0000 & 0.0000 & 0.0000 & 0.0000 \\ 0.3393 & 0.4466 & 0.0000 & 0.0000 & 0.0000 \\ 0.1448 & 0.3393 & 0.4466 & 0.0000 & 0.0000 \\ 0.0474 & 0.1448 & 0.3393 & 0.4466 & 0.0000 \\ 0.0127 & 0.0474 & 0.1448 & 0.3393 & 0.4466 \\ 0.0051 & 0.0127 & 0.0474 & 0.1448 & 0.3393 \end{vmatrix} \begin{vmatrix} b0 \\ b1 \\ b2 \\ b3 \\ b4 \end{vmatrix} = \begin{vmatrix} 0.2748 \\ 0.3392 \\ 0.2205 \\ 0.1025 \\ 0.0395 \\ 0.0160 \end{vmatrix}$$

Using a spreadsheet program (Excel®), the output of such a multiple linear regression is shown below in Table 3 and the coefficients represent the distribution of mass isotopomers due to deuterium incorporation.

TABLE 3

Regression output from Excel ® spreadsheet program

| Intercept | Co-efficients | Standard Error | t Stat | P-value | Predicted coefficients |
|---|---|---|---|---|---|
| X Variable 1 | 0.6154 | 0.0030 | 205.5862 | 0.0031 | 0.6027 |
| X Variable 2 | 0.2919 | 0.0038 | 77.6582 | 0.0082 | 0.3091 |
| X Variable 3 | 0.0727 | 0.0038 | 18.9608 | 0.0335 | 0.0753 |
| X Variable 4 | 0.0138 | 0.0038 | 3.6419 | 0.1706 | 0.0116 |
| X Variable 5 | 0.0078 | 0.0031 | 2.5213 | 0.2404 | 0.0013 |

Thus 61.5% of the molecules did not have any deuterium, 29.2% were labeled with one deuterium and 7.3% labeled with 2 deuterium atoms. Using the ratio of consecutive isotopomers relationship that $m2/m1=(N(d)-1)/2 \times p/(1-p)$, we determined the theoretical N(d) to be 20. The theoretical deuterium isotopomers of (20, 0.025) are (0.6027, 0.3091, 0.0753, 0.0116, 0.0013) corresponding to fractions of molecules with 0, 1, 2, 3, and 4 deuterium substitution. This is the theoretical distribution of deutertium isotopomers in the newly synthesized protein. It can be shown by multiple linear regression that observed distribution (X1, X2, X3 . . . ) accounts for 96.2% of the deuterium distribution in m/z 1393 or the new fraction is 0.9619.

M2/m1 ratios were determined similarly for the other peptides. The corresponding theoretical distributions were calculated. The new fraction of the peptide is the contribution of the theoretical distribution as a fraction of the observed d-isotopomer distribution.

Table 4 shows the normalized spectra of peptides isolated from serum after 8 days of deuterated water treatment (labeled peptides). The respective new fractions were calculated using the algorithm previously described.

EXAMPLE III

Determination of New Fraction When Isotopomer Distribution of the Fully Labeled Peptide is Known The fraction of new protein can also be determined from the peptide spectrum when the spectra of the "labeled" and "unlabeled" peptides are known. In the example of AMP deaminase, it was found that the protein was almost completely labeled (100% new synthesis) by day 8 of deuterium water treatment. Protein fractions containing albumin and

TABLE 4

Mass isotopomer distributions of the identified peptides after deuterium labeling

|  | m/z 1299 | m/z 1393 | m/z 1479 | m/z 1609 | m/z 1681 |
|---|---|---|---|---|---|
| M0 | 0.3409 ± 0.0089 | 0.2748 ± 0.0044 | 0.2672 ± 0.0073 | 0.2757 ± 0.0026 | 0.2216 |
| M1 | 0.3418 ± 0.0061 | 0.3392 ± 0.0090 | 0.3159 ± 0.0127 | 0.3266 ± 0.0120 | 0.2902 |
| M2 | 0.1931 ± 0.0084 | 0.2205 ± 0.0063 | 0.2089 ± 0.0023 | 0.2266 ± 0.0028 | 0.2343 |
| M3 | 0.0726 ± 0.0110 | 0.1025 ± 0.0028 | 0.1201 ± 0.0073 | 0.1082 ± 0.0057 | 0.1325 |
| M4 | 0.0192 ± 0.0023 | 0.0395 ± 0.0014 | 0.0550 ± 0.0030 | 0.0451 ± 0.0044 | 0.0652 |
| M5 | 0.0133 ± 0.0056 | 0.0160 ± 0.0022 | 0.0329 ± 0.0072 | 0.0178 ± 0.0042 | 0.0284 |
| Average Mass | 1300.4942 | 1394.7257 | 1480.9391 | 1610.7292 | 1683.2361 |
| Δ mass | 0.3594 | 0.4783 | 0.522 | 0.3211 | 0.3472 |
| N(d) | 21 | 20 | 30 | 17 | 22 |
| New Fraction | 0.6960 ± 0.0827 | 0.9618 ± 0.0158 | 0.6994 ± 0.0442 | 0.7380 ± 0.0131 | 0.6326 ± 0.0602 |

The averages and standard deviations were calculated from triplicate MADI-TOF analyses. It is noted that there was only one analysis for the peak at m/z 1681. Average mass was calculated according to Blom. The change in average mass is given by N(d) × p × (New Fraction).

The incorporation of deuterium in these peptides results in small shifts in the average mass. The magnitude of the shift due to deuterium incorporation depends on the enrichment in water, the number of non-essential amino acids and the fraction of new protein. The fraction of new protein was calculated using the inverse concatenation operation described herein. Since the operation utilizes information from all spectral peaks, an estimate of the accuracy (standard deviation) can be obtained from a single spectrum in m/z 1681. From the magnitude of mass shift and the calculated new fraction, the number of possible deuterium substitution (N(d)) can be estimated. N(d) is the theoretical number of deuterium atoms incorporated when deuterated water enrichment is 100%. It is to be expected that peptides of the same protein have the same synthesis rate and new fraction, which is shown in the albumin peptides in Table 2. Peptides from other proteins may have different synthesis rates and have different new fractions.

AMP deaminase from sera obtained before deuterium labeling and on day 8 after deuterium labeling were mixed in to simulate 10, 25, 50 and 75% synthesis. The different mixtures were subject to trypsin digest and MALDI-TOF analysis. The observed spectra are shown in Table 4. Using multiple linear regression analysis, the coefficients for "labeled" and "unlabeled" peptides that would give the observed distributions were determined. The coefficient representing percent synthesis and its standard deviation were provided by the regression analysis (Table 5). This example represents a special case of the application of the mass isotopomer analysis method. The technique disclosed differs from that of Vogt in that the calculation of average mass is not required, and the mass isotopomer distribution data is used in the multiple linear regression analysis. It should be noted that it is uncommon to find proteins that are fully labeled (100% newly synthesized). The salient feature of the technique disclosed herein is that the knowledge of the labeling of the 100% newly synthesized protein is not required.

TABLE 5

Determination of percent synthesis using "labeled" and "unlabeled" spectra and multiple linear Regression Analysis

|  | Unlabeled | 10% Labeled | 25% Labeled | 50% Labeled | 75% Labeled | 100% Labeled |
|---|---|---|---|---|---|---|
| M0 | 0.4466 ± 0.0101 | 0.4333 ± 0.0072 | 0.4061 ± 0.0106 | 0.3550 ± 0.0106 | 0.3054 ± 0.0106 | 0.2748 ± 0.0044 |
| M1 | 0.3393 ± 0.0047 | 0.3402 ± 0.0036 | 0.3360 ± 0.0222 | 0.3280 ± 0.0106 | 0.3247 ± 0.0106 | 0.3392 ± 0.0090 |
| M2 | 0.1448 ± 0.0024 | 0.1574 ± 0.0014 | 0.1667 ± 0.0082 | 0.1813 ± 0.0106 | 0.1963 ± 0.0106 | 0.2205 ± 0.0063 |
| M3 | 0.0474 ± 0.0110 | 0.0549 ± 0.0021 | 0.0576 ± 0.0037 | 0.0774 ± 0.0106 | 0.0958 ± 0.0106 | 0.1025 ± 0.0028 |
| M4 | 0.0127 ± 0.0044 | 0.0095 ± 0.0038 | 0.0179 ± 0.0026 | 0.0309 ± 0.0106 | 0.0459 ± 0.0106 | 0.0395 ± 0.0014 |
| M5 | 0.0051 ± 0.0025 | 0.0047 ± 0.0029 | 0.0157 ± 0.0094 | 0.0208 ± 0.0106 | 0.0249 ± 0.0106 | 0.0160 ± 0.0022 |
| % Synthesis | — | 15.4 ± 6.8 | 25.6 ± 7.1 | 47.8 ± 3.5 | 68.6 ± 1.5 | — |

Protein fractions containing albumin and AMP deaminase from sera obtained before deuterium labeling and on day 8 after deuterium labeling were mixed in to simulate 10, 25, 50 and 75% synthesis. The averages and standard deviations of peptide m/z 1393 were calculated from triplicate MADI-TOF analyses for the different mixtures.

EXAMPLE IV

Measuring Protein Synthesis Using $^{15}$N Amino Acid Labeling in Pancreas Cancer Cells—Illustrating the Application of the Concatenation Function Quantitative analysis of mass spectrum would be simple if there were no naturally existing isotopes. The existence of isotopes of carbon ($^{13}$C), hydrogen ($^2$H), nitrogen ($^{15}$N), oxygen ($^{18}$O) and sulfur ($^{33}$S, $^{34}$S) presents challenges to the interpretation of mass spectrum and opportunities for using these isotopes for biological investigations. The presence of different amount of isotopes in molecules of a protein generates molecules with different masses. These molecules of the same compound with different molecular weights form the family of mass isotopomers. The distribution of mass isotopomers gives rise to the appearance of the isotope envelop observed in a peptide spectrum.

Isotopomer distribution of a peptide is predominantly influenced by the number of carbon, nitrogen and hydrogen atoms in the molecule and the isotopic abundance of each species. In a peptide where the natural abundances of $^{15}$N, $^{18}$O and $^2$H are relatively low compared to that of $^{13}$C, the isotopomer distribution can be approximated by a binomial distribution governed by $N_C$ and p, the number of carbon atoms and its natural abundance. The individual relative intensity of isotopomer (n) is given by the following equation:

$$M(n)=(N_C!/n!(N_C-n)!)p^n(1-p)^{N_C-n}$$

In this formula, n stands for the number of $^{13}$C atoms and $N_C$ stands for the total number of carbon atoms in the peptide. The individual intensity is given by $M_0=(1-p)^N$, $M_1=Np\times(1-p)^{N-1}$, etc.; and the sum of these individual intensities is equal to 1. This distribution can be determined experimentally by normalizing individual intensity by the total intensity such that the sum of normalized intensities equals to 1. The normalized intensity is given the name of RIA (relative isotopologue abundance) in the paper by Vogt (2003) and Vogt (2005). A consequence of a normalized distribution is that the sum of product of M(n)×n, which we defined as ΣMn, (Lee et al., Am J Physiol 1994, 266, E699-E708.) has the meaning of average mass. When the contribution of natural abundance is removed, ΣMn also has the same meaning as #isotope atom/molecule, the equivalent of specific activity. For a binomial distribution, ΣMn=N×p.

When a peptide has two populations of isotopes $^{13}$C and $^{15}$N as in the case of the instant example, the distribution of isotopomer is not given by a binomial distribution. When the presence or absence of $^{13}$C is independent of the presence or absence of $^{15}$N and vice versa, the distribution is the concatenation of isotopomers from these stable isotope species. That is, the observed isotopomer distribution of the peptide is the concatenation of a binomial distribution of $^{13}$C isotopomers governed by ($N_C$, p) and a binomial distribution of $^{15}$N isotopomers governed by ($N_N$, p'). The mathematical operation of the concatenation function is as follows: If C-distribution is ($a_0, a_1, a_2, a_3, \ldots, a_n$), N-distribution is ($b_0, b_1, b_2, b_3, \ldots, b_n$), and combined distribution is ($c_0, c_1, c_2, c_3, \ldots c_n$), then newly synthesized distribution using concatenation operation is $c_0=a_0b_0$; $c_1=a_0b_1+a_1b_0$; $c_2=a_0b_2+a_1b_1+a_2b_0$; $c_3=a_0b_3+a_1b_2+a_2b_1+a_3b_0$. As a result, the average mass of the peptide is the sum of average mass of these $^{13}$C and $^{15}$N distributions as follows:

$$\Sigma Mn=N_C\times p+N_N\times P'$$

Figure 14:
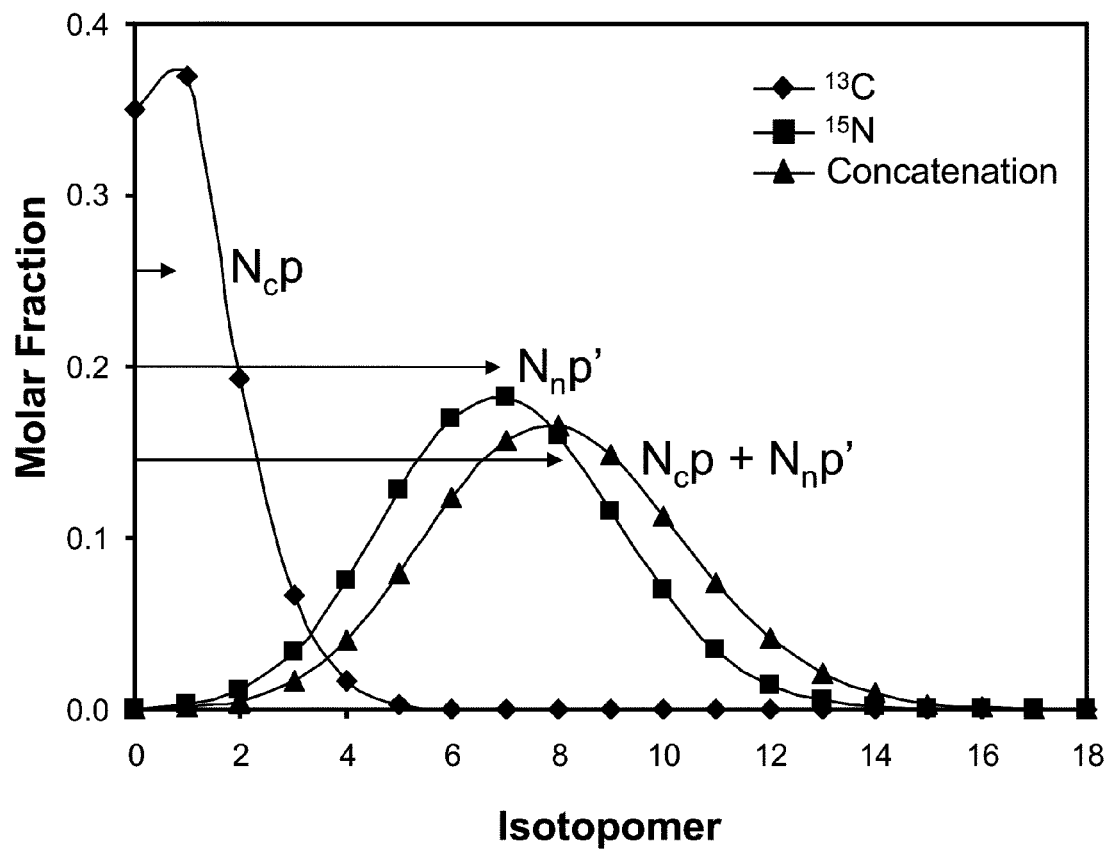
FIG. 14 shows isotope envelopes of two theoretical mass isotopomer distributions ($^{13}C$ and $^{15}N$) and the concatenation of these two distributions giving rise to a third distribution. The means of these two distributions are $N_c p$ and $N_n p'$. The mean of the new distribution as the result of concatenation is $N_c p + N_n p.'$

The combined distribution of a peptide containing $^{13}$C and $^{15}$N isotopomers and its implication on changes in average mass (mass shift) is illustrated in FIG. 14. In particular, FIG. 14 illustrates the isotope envelopes of three theoretical mass isotopomer distribuations showing effect of concatenation. The first curve is that of the distribution of $^{13}$C isotopomers calculated from a binomial distribution assuming carbon number to be 94 and natural enrichment of $^{13}$C to be 0.0111. The second curve represents the distribution of $^{15}$N isotopomers with nitrogen number of 21 and enrichment of 0.333. The third curve is that of concatenation of these two distributions representing the newly synthesized protein after incorporation of $^{15}$N. The sum of molar fractions for each curve is 1.

The $^{13}$C isotopomer distribution of a hypothetical natural peptide and $^{15}$N isotopomer distribution of a labeled peptide are typical binomial distributions (see FIG. 14). The mean and variance of the $^{13}$C isotopomer distribution around the monoisotopic peak ($m_0$) are $N_C p$ and $N_C p(1-p)$ respectively, where $N_C$ is the number of carbon atoms in the peptide, and p is the natural abundance of $^{13}$C. Similarly, the mean and variance of the $^{15}$N isotopomer distribution are $N_N p'$ and $N_N p'(1-p')$ respectively and p' is the average $^{15}$N enrichment. The isotopomer distribution after concatenation is also shown in FIG. 14. The mean and variance of the new distribution is given by $(N_C p+N_N p')$ and $[N_C p(1-p)+N_N p'(1-p')]$ respectively. The mass shift of the new distribution is $[(N_C p+N_N p')-N_C p]=N_N p'$. Therefore, the mass shift or the change in average mass of a peptide is a function of the $^{15}$N isotopomer distribution.

The observed spectrum of a peptide (both preexisting and newly synthesized) is then the linear combination of isotopomers of natural (unlabeled) and the expected labeled peptides, and the ratio of labeled to the total isotopomers provides a molar fraction of the newly synthesized protein as follows:

$$\Sigma Mn=N_C\times p+\text{FSR}\times(N_N\times p')$$

$$\Delta \text{average mass}=\Sigma Mn-N_C\times p-\text{FSR}\times(N_N\times p')$$

Since $N_C\times p$ is given by the unlabeled peptide, FSR can be determined when $N_N\times p'$ is known. $N_N\times p'$ can also be determined in a peptide whose FSR is 1 (100%). In the method of Vogt (2003) using [U$^{13}$C$_6$]-glucose as the source of isotope, the theoretical change in average mass is $\Sigma N_i \Delta k_i$, where $N_i$ is the number of amino acid (i) and $\Delta k_i$ is the change in average mass of that amino acid (i) after labeling. $\Delta k_i$ is determined from peptides with FSR close to 100% and their amino acid sequences.

Because $N_N$ can be determined from the known peptide sequence, the $^{15}$N enrichment (p') can be determined by curve fitting (mass shift/$N_N$). The mass shift is first obtained by inspection. Its value is changed by small increment or decrement to arrive at a new p' such that the ratio of the theoretical M(i) based on the binomial distribution ($N_N$, p') to the observed M(i) in regions with no overlap from the unlabeled spectrum is constant. Once the natural isotopomers and the $^{15}$N isotopomers are known, the isotopomers of the $^{13}$C and $^{15}$N labeled peptide can be constructed using the concatenation operation. The resultant distribution is the expected distribution of the new peptide and can be used to determine newly synthesized fraction. This approach obviates the need for determining $\Delta k_i$ in peptides with FSR close to 100% as required in the method of Vogt (2003).

First, the intensity distribution of individual peaks in the peptide without labeling (control) is normalized. After normalization, formula $M_1/M_0=N\times p/(1-p)$ (p=0.0111) is used to calculate the carbon atoms by assuming $^{13}C$ natural abundance to be 1.11%. Once the $N_C$ and p are known, a binomial distribution is set up following the formula: intensity of isotopomer $(n)=(N_C!/n!(N_C-n)!)p^n(1-p)^{Nc-n}$. In this formula, n stands for the number of $^{13}C$ atoms and $N_C$ stands for the total number of carbon atoms in the peptide. An example of such computation is shown in Table 6. The theoretical carbon number is somewhat larger than the number calculated from peptide sequence due to other minor natural enrichments, like $^2H$, $^{18}O$, $^{15}N$, and $^{33}S$. In fact, the natural distribution is a concatenation of all these distributions. The approximation of the observed distribution by the theoretical distribution of $^{13}C$ suggests that the mass isotopomer distribution is predominantly influenced by natural abundance of $^{13}C$ and validate the use of binomial model for interpretation of peptide spectrum.

Both 50% and 33% of artificial enrichment of $^{15}N$ in the medium cause obvious mass shift in spectrum distribution. The mass shift of the labeled spectrum can be determined from the change in average mass after subtracting the natural spectrum. Based on the mass shift and the number of nitrogen atoms in the specific fragment (from sequence information), the average $^{15}N$ enrichment can be deduced. After the $N_N$ and p' are known, the theoretical $^{15}N$ isotopomer distribution can be generated based on a binomial distribution function (see Tables 7 and 8). The concatenation of $^{13}C$ (Table 6) and $^{15}N$ distributions (Tables 7 and 8) represents isotopomer distribution of the newly synthesized peptide. It is important to note that the sum of all isotopomers in any distribution, C-isotopomer, N-isotopomer or the concatenated isotopomer, is equal to 1.

The observed isotopomer distribution of a peptide is the weighted sum of isotopomers of the natural (preexisting) and the labeled (new) peptide. By multiple linear regression analysis using the observed distribution as the dependent variable and the preexisting and newly synthesized parts as the independent variables, the contribution of each of preexisting and new peptides can be determined.

TABLE 6

The unlabeled spectrum of 1699 m/z in spot 6 can be simulated by a binomial distribution.

| | peak intensity | Normalized | $M_1/M_0$ | carbon #[a] | Theoretical distribution[b] |
|---|---|---|---|---|---|
| $M_0$ | 57603.5 | 0.347 | 1.044 | 94.1 | 0.350 |
| $M_1$ | 60153.5 | 0.363 | | | 0.370 |
| $M_2$ | 31848.5 | 0.192 | | | 0.193 |
| $M_3$ | 11834.5 | 0.071 | | | 0.066 |
| $M_4$ | 3415.5 | 0.021 | | | 0.017 |
| $M_5$ | 749.5 | 4.5E−03 | | | 3.4E−03 |
| $M_6$ | 198.5 | 1.2E−03 | | | 5.7E−04 |
| $M_7$ | 82.5 | 5.0E−04 | | | 8.0E−05 |

[a]The carbon number calculation was based on the formula $M_1/M_0 = N \times p/(1-p)$, p = 0.0111.
[b]Binomial distribution was based on N = 94, p = 0.0111.

TABLE 7

Determining the expected distribution of the newly synthesized protein based on peptide spectrum from 50% $^{15}N$ labeling using concatenation operation.

| m/z | Peak intensity | Normalize | $^{15}N$ binomial[a] | Concatenation process[b] | | | | | Expected Newly synthesized[c] |
|---|---|---|---|---|---|---|---|---|---|
| $M_0$ | 31808.5 | 0.096 | 2.0E−04 | 7.0E−05 | | | | | 7E−05 |
| $M_1$ | 36121.5 | 0.109 | 0.002 | 0.001 | 7.3E−05 | | | | 8.0E−04 |
| $M_2$ | 19490.5 | 0.059 | 0.011 | 0.004 | 0.001 | 3.8E−05 | | | 0.004 |
| $M_3$ | 9941.5 | 0.030 | 0.033 | 0.012 | 0.004 | 4.0E−04 | 1.4E−05 | | 0.016 |
| $M_4$ | 11476.5 | 0.035 | 0.075 | 0.026 | 0.012 | 0.002 | 1.5E−04 | 4.1E−06 | 0.040 |
| $M_5$ | 20352.5 | 0.062 | 0.127 | 0.044 | 0.027 | 0.006 | 0.001 | 4.3E−05 | 0.079 |
| $M_6$ | 30234.5 | 0.092 | 0.170 | 0.059 | 0.046 | 0.014 | 0.002 | 2.2E−04 | 0.122 |
| $M_7$ | 34092.5 | 0.103 | 0.182 | 0.063 | 0.062 | 0.024 | 0.005 | 0.001 | 0.155 |
| $M_8$ | 33282.5 | 0.101 | 0.159 | 0.055 | 0.066 | 0.033 | 0.009 | 0.002 | 0.165 |
| $M_9$ | 32893.5 | 0.100 | 0.115 | 0.040 | 0.058 | 0.035 | 0.012 | 0.003 | 0.148 |
| $M_{10}$ | 27913.5 | 0.084 | 0.069 | 0.024 | 0.042 | 0.031 | 0.013 | 0.003 | 0.113 |
| $M_{11}$ | 20675.5 | 0.063 | 0.035 | 0.012 | 0.025 | 0.022 | 0.011 | 0.004 | 0.075 |
| $M_{12}$ | 13205.5 | 0.040 | 0.014 | 0.005 | 0.013 | 0.013 | 0.008 | 0.003 | 0.043 |
| $M_{13}$ | 6398.5 | 0.019 | 0.005 | 0.002 | 0.005 | 0.007 | 0.005 | 0.002 | 0.022 |
| $M_{14}$ | 2392.5 | 0.007 | 0.001 | 4.9E−04 | 0.002 | 0.003 | 0.002 | 0.001 | 0.010 |
| $M_{15}$ | 70.5 | 2.1E−04 | 3.3E−04 | 1.2E−04 | 0.001 | 0.001 | 0.001 | 0.001 | 0.004 |

[a]$^{15}N$ binomial distribution was based on N = 21 (from peptide chemical structure), p = 0.333 (calculated from equation (mass shift = Np). For mass shift of 7, p = 7/21 = 0.333).
[b]Concatenation was done based on $^{13}C$ (Table 6) and $^{15}N$ binomial distributions.
[c]The calculation of the newly synthesized protein is performed by regression of the normalized observed distribution (column 3) against the normalized intensity of individual peaks in the peptide without labeling (control from Table 6) and the expected isotopomer distribution of the newly formed peptide (column 10). The normalization converts the individual intensity to relative intensity with the sum of intensities of all peaks equal to 1.

TABLE 8

Determining the expected distribution of the newly synthesized protein based on peptide spectrum from 33% $^{15}N$ labeling using concatenation operation.

| m/z | Peak intensity | Normalize | $^{15}N$ binomial | Concatenation process | | | Expected Newly synthesized |
|---|---|---|---|---|---|---|---|
| $M_0$ | 29743 | 0.089 | 0.006 | 0.002 | | | 0.002 |
| $M_1$ | 34353 | 0.102 | 0.036 | 0.013 | 0.002 | | 0.015 |

TABLE 8-continued

Determining the expected distribution of the newly synthesized protein based on peptide spectrum from 33% $^{15}$N labeling using concatenation operation.

| m/z | Peak intensity | Normalize | $^{15}$N binomial | Concatenation process | | | | | Expected Newly synthesized |
|---|---|---|---|---|---|---|---|---|---|
| $M_2$ | 28029 | 0.083 | 0.099 | 0.034 | 0.013 | 0.001 | | | 0.049 |
| $M_3$ | 29876 | 0.089 | 0.170 | 0.059 | 0.036 | 0.007 | 4.5E−04 | | 0.102 |
| $M_4$ | 41305 | 0.123 | 0.209 | 0.073 | 0.062 | 0.019 | 0.003 | 1.3E−04 | 0.156 |
| $M_5$ | 46585 | 0.139 | 0.194 | 0.067 | 0.076 | 0.033 | 0.007 | 7.4E−04 | 0.184 |
| $M_6$ | 42364 | 0.126 | 0.141 | 0.049 | 0.070 | 0.040 | 0.012 | 0.002 | 0.174 |
| $M_7$ | 31863 | 0.095 | 0.082 | 0.029 | 0.051 | 0.037 | 0.015 | 0.004 | 0.136 |
| $M_8$ | 23328 | 0.069 | 0.039 | 0.014 | 0.030 | 0.027 | 0.014 | 0.004 | 0.090 |
| $M_9$ | 15770 | 0.047 | 0.016 | 0.005 | 0.014 | 0.016 | 0.010 | 0.004 | 0.051 |
| $M_{10}$ | 9021 | 0.027 | 0.005 | 0.002 | 0.006 | 0.008 | 0.006 | 0.003 | 0.025 |
| $M_{11}$ | 3545 | 0.011 | 0.001 | 4.8E−04 | 0.002 | 0.003 | 0.003 | 0.002 | 0.011 |
| $M_{12}$ | 108 | 3.2E−04 | 3.1E−04 | 1.1E−04 | 0.001 | 0.001 | 0.001 | 0.001 | 0.004 |
| $M_{13}$ | 59 | 1.8E−04 | 5.9E−05 | 2.1E−05 | 1.1E−04 | 2.7E−04 | 3.6E−04 | 3.2E−04 | 0.001 | a) The calculation is the same as in Table 7 except for mass shift being 4.5 and p = 4.5/21 = 0.224.

Figure 15:
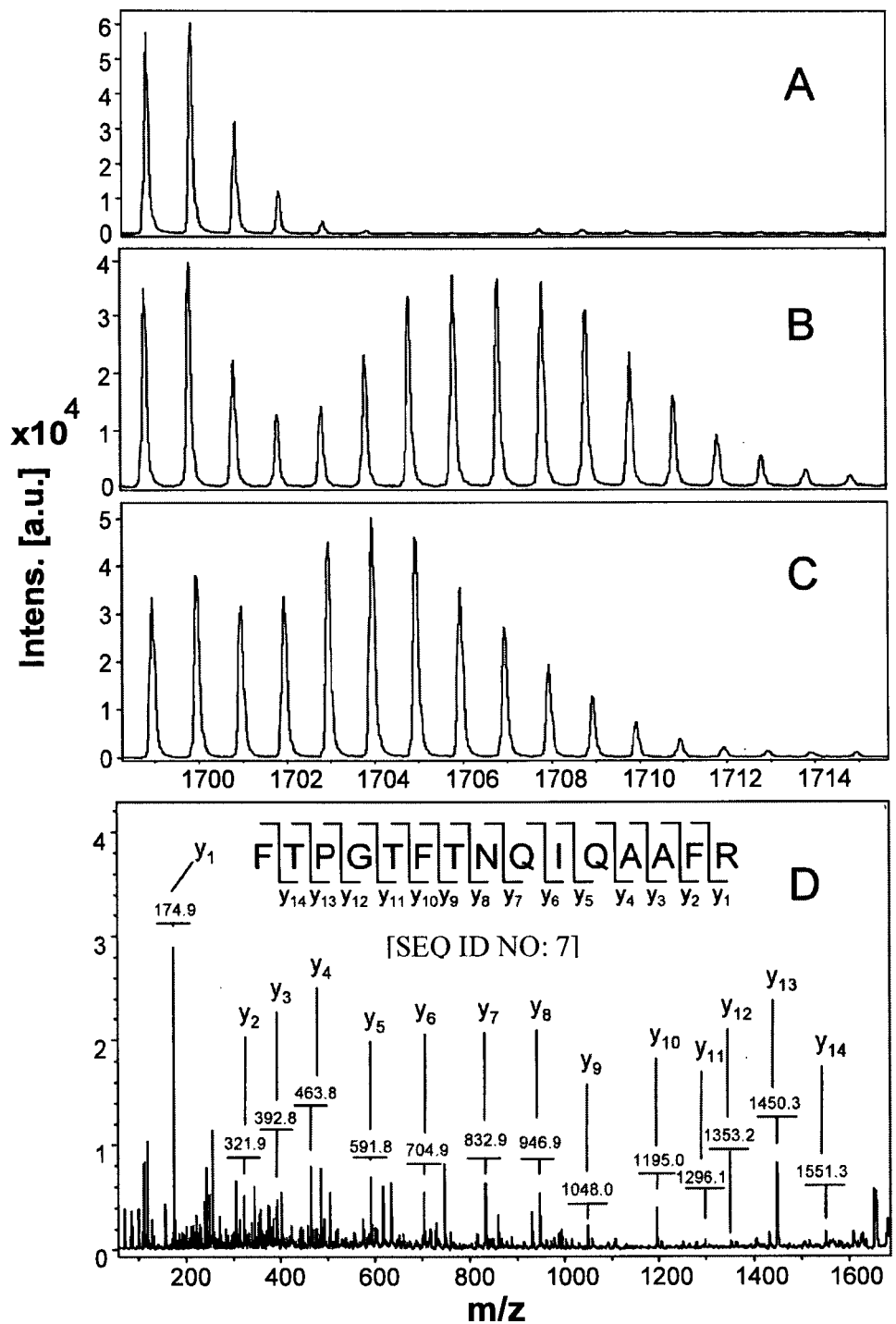
FIG. 15 shows three mass spectra of 1699 m/z fragment from spot 6 of lysates of cells grown in the presence of natural amino acids (Panel A), 50% enriched (Panel B) and 33% enriched (Panel C) $^{15}$N algal amino acid mixtures.

The effect of $^{15}$N enrichment on the isotopomer distribution of a peptide is illustrated in FIG. 15. In particular, FIG. 15 illustrates mass spectra of 1699 m/z fragment from spot 6 of lysates of cells grown in the presence of natural amino acids (Panel A), 50% enriched (Panel B) and 33% enriched (Panel C) $^{15}$N algal amino acid mixtures. The MS/MS spectrum of this fragment used for protein identification is shown in Panel D. Panel A shows the distribution of unlabeled (natural) fragment from control medium. The spectrum in Panel B is from the same peptide obtained from cells grown in 50% $^{15}$N enriched medium, showing the obvious spectrum shift in mass. The spectrum of Panel C is from the same peptide obtained from cells grown in 33% $^{15}$N enriched medium, which shows smaller mass shift than that of 50% $^{15}$N enrichment. Since the number of nitrogen atoms in the peptides is the same, the difference in mass shift reflects the difference in $^{15}$N enrichment in the medium. The 50% $^{15}$N labeling caused an almost complete separation of the isotopomers of the natural peptide from the distribution of the peptide of newly synthesized fraction. There is, however, still some overlapping of these two parts in the treatment of 33% $^{15}$N labeling (see Panel C).

As is illustrated by the above discussion, a ratio of newly synthesized protein may be determined by using the concatenation operations disclosed herein. Specifically, where the newly synthesized peptide has many peaks that overlap with those of the pre-existing peptide (see FIG. 7) the inverse concatenation operation may be used and where overlap is minimal (see FIG. 15) the concatenation operation may be used.

In one embodiment, a processor may be used to determine a ratio of a new protein and a pre-existing protein (a protein turnover rate) from mass spectra data after enzyme digestion. The ratio may be used to predict an outcome (i.e., risk or benefit) of a therapeutic intervention such as a drug treatment. For example, a protein turnover rate of a cancer cell of a human or other animal patient may be determined in the presence of a drug treatment. If the protein turnover rate is found to be suppressed upon the administration of the drug treatment, a prediction can be made that the drug treatment may be effective. Such a prediction of an outcome may be done by the processor by, for example, providing the processor (e.g., a memory associated with the processor) a baseline value for a determined protein turnover ratio. In one method, the processor determines a protein turnover ratio as described above and compares that ratio to a baseline value associated with the processor. In the example of a protein turnover ratio in a cancer cell, if the determined protein turnover ratio is less than the baseline value, the processor predicts a beneficial outcome for the drug treatment associated with the suppressed protein turnover ratio. A processor may also be used in a similar manner to differentiate protein secreted by normal cells from malignant cells by, for example, comparing a rate of secretion in the presence of a drug treatment.

As is clear from the above discussion, a method or a machine readable medium embodying a method may be performed or embodied in any number of devices, including but not limited to a desktop computer, a portable computer, handheld processing device, or a processor associated with a mass spectrometer. In embodiments describing implementation with a keypad, a suitable keypad may include, but is not limited to, a QWERTY keypad, a numerical keypad, a letter keypad, an alphanumeric keypad, a symbolic keypad, or an alphanumeric-symbolic keypad having physically depressible keys or touch-screen response.

Some portions of the detailed description above are presented in terms of algorithms and symbolic representations of operations on data bits within a computer memory. One example is an algorithm to calculate a newly synthesized protein fraction from intensities of mass peaks of labeled and heavy proteins. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be born in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing," "computing," "generating," "determining," "selecting," "displaying," "collecting," "constructing," "updating," "modifying," "assigning," "requesting," "computing," "performing," "granting," "using," or the like, refer to the actions and processes of a computer system, or similar electronic computing/processing device that manipulates and transforms data represented as physical (electronic) quantities within a computer system's registers and memories into other data similarly represented as physical quantities within the computer system memories, registers or other such information storage, transmission or display devices.

The invention also relates to an apparatus for performing the operations herein. This apparatus may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards or any type of media suitable for storing electronic instructions, each of which may be connected to a computer system bus.

In the preceding detailed description, specific embodiments and examples are illustrated. It will, however, be evident that various modifications and changes may be made thereto without departing from the broader spirit and scope of the invention as set forth in the claims. The specification and drawings are, accordingly, to be regarded in an illustrative rather than a restrictive sense.

The invention claimed is:

1. A method comprising:
using a processor, determining a protein turnover ratio in a cell associated with cancer based on a newly synthesized and a pre-existing fraction of a protein from a mass spectra of a peptide produced by enzyme digestion of the protein before and after isotope labeling, wherein the resultant spectra are presented as integrated peak heights of a corresponding mass to charge ratio in a centroid mode; and
predicting an outcome of a therapeutic intervention associated with cancer based on changes in the protein turnover ratio,
wherein non-essential amino acids of the-newly synthesized protein arc labeled with an isotope with low abundance through metabolism of the amino acids, an average enrichment of which is determined from the peptide containing such isotopically labeled amino acids and isotope labeling comprises introducing one of $^{13}C$, $^{15}N$ in the form of $^{15}N$ or $^{13}C$ amino acids, $^{13}C$ in the form of [$U^{13}C$]-glucose,[$^{13}C$]-lactate or [$^{13}C$]-acetate into the non-essential amino acids.

2. The method of claim 1 further comprising determining protein turnover of protein separated by gel-electrophoresis, ion-exchange chromatography, molecular sizing chromatography, immuno-isolation method, protein-affinity column/chip or any combinations of these techniques.

3. The method of claim 1 further comprising determining protein synthesis and a turnover of proteins in cells or tissues of living organisms.

4. The method of claim 3 wherein the protein synthesis or the turnover of proteins comprises proteins selected From the group consisting of nuclear proteins, membrane proteins, membrane receptors, cell skeleton proteins, growth factors, peptide hormones, mitochondrial proteins, immunoglobulins, cytokines and intracellular signaling molecules.

5. The method of claim 3 further comprising detecting changes in turnover of proteins that perform biological. functions in response to nutrients, hormones or drugs.

6. The method of claim 1, wherein determining the newly synthesized and pre-existing fractions of the protein comprises:
determining a spectrum of an unlabeled protein of interest;
determining a spectrum of the protein from cells after isotope incorporation during its synthesis;
mathematically using an inverse concatenation operation to remove the unlabeled protein spectrum from the isotopically labeled newly synthesized protein to determine the observed mass isotopomer distribution resulting from the isotope labeling;
determining the average isotope enrichment in amino acids from mass isotopomer distribution resulting from the isotope labeling according to a binomial distribution;
constructing a theoretical mass isotopomer distribution of the newly synthesized protein using the determined average isotope enrichment in amino acids; and
comparing the observed mass isotopomer distribution and the theoretical mass isotopomer distribution using regression analysis to determine a ratio of the newly synthesized protein and the pre-existing protein as the newly synthesized fraction of the protein.

7. The method of claim 1, wherein isotope enrichment of the newly synthesized protein is 50 percent or less.

* * * * *

UNITED STATES PATENT AND TRADEMARK OFFICE
CERTIFICATE OF CORRECTION

PATENT NO. : 8,574,543 B2
APPLICATION NO. : 12/333240
DATED : November 5, 2013
INVENTOR(S) : Wai-Nang P. Lee and Guishan Xiao Page 1 of 1

It is certified that error appears in the above-identified patent and that said Letters Patent is hereby corrected as shown below:

In the Claims

Column 27, Claim 1, line 44, please delete "the-newly" and insert --the newly--.

Column 27, Claim 4, line 62, please delete "From" and insert --from--.

Signed and Sealed this
Twenty-eighth Day of January, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,574,543 B2  
APPLICATION NO. : 12/333240  
DATED : November 5, 2013  
INVENTOR(S) : Wai-Nang P. Lee and Guishan Xiao Page 1 of 1

It is certified that error appears in the above-identified patent and that said Letters Patent is hereby corrected as shown below:

In the Claims
Column 27, Claim 1, line 45, please delete "arc" and insert --are--.

Signed and Sealed this
Twenty-fifth Day of March, 2014

Michelle K. Lee
*Deputy Director of the United States Patent and Trademark Office*